United States Patent [19]

Bruneteau et al.

[11] Patent Number: 4,981,618

[45] Date of Patent: Jan. 1, 1991

[54] SPHINGOPHOSPHOLIPIDS CONTAINING INOSITOL, THEIR PRODUCTION, AND THEIR APPLICATION AS INDUCERS OF RESISTANCE TO VARIOUS CRYPTOGAMIC DISEASES IN PLANTS

[75] Inventors: Maud Bruneteau, Tassin; Paul-Michel Molot, Caumont Sur Durance; Thadee Staron, Noisy-Le-Roi; Olivier Lhomme, Lyon; Pierre Mas, St-Saturnin-Les-Avignon, all of France

[73] Assignees: Institut National de la Recherche Agronomique (INRA), Paris; Centre National de la Recherche Scientifique, Paris, both of France

[21] Appl. No.: 315,302

[22] Filed: Feb. 24, 1989

[30] Foreign Application Priority Data

Oct. 6, 1988 [FR] France .................. 88 13130

[51] Int. Cl.$^5$ ............................................. C07F 9/02
[52] U.S. Cl. ............................................. 260/403
[58] Field of Search ................................. 260/403

[56] References Cited

U.S. PATENT DOCUMENTS 3,704,254 11/1972 Aveja .................. 260/403

Primary Examiner—Mukund J. Shah
Assistant Examiner—C. L. Cseh
Attorney, Agent, or Firm—Berman, Aisenberg & Platt

[57] ABSTRACT

These compounds, represented by the formula (I) below, are used by way of agents inducing resistance to cryptogamic diseases in plants capable of being infested by a pathogenic fungus, for example, for the protection of wheat especially with respect to *Septoria nodorum*, *Erysiphe graminis* and *Gaemannomyces graminis*; of capsicum with respect to *Phytophthora capsici*; of melon with respect to *Pseudoperonospora cubensis*; of tomato with respect to *Phytophthora infestans*; and of "Xanthi" tobacco with respect to *Phytophthora parasitica* var. *nicotianae*.

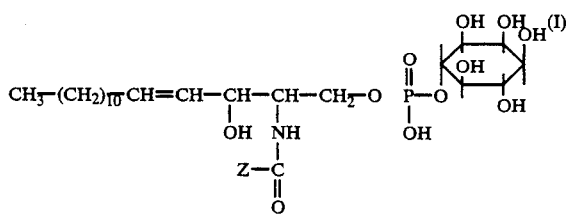

in which Z denotes the residues

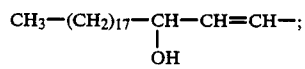

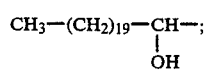

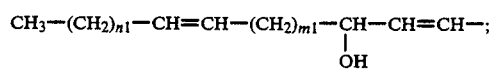

with $0 \leq n1 \leq 15$; $0 \leq m1 \leq 15$ and $n1+m1=15$; and $CH_3-(CH_2)_{n2}-CH-(CH_2)_{m2}-$, with $0 \leq n2 \leq 18$; $0 \leq m2 \leq 18$, and $n2+m2=18$.

9 Claims, 20 Drawing Sheets

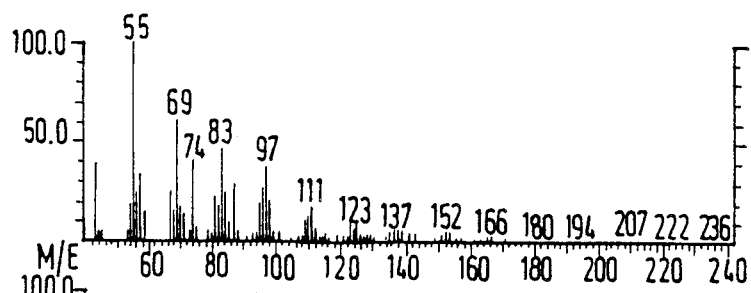
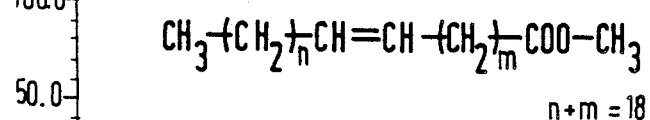
FIG.8c
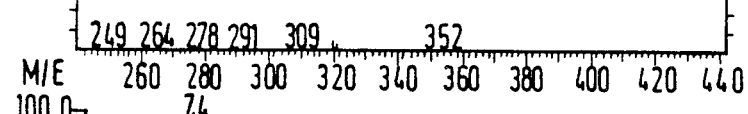
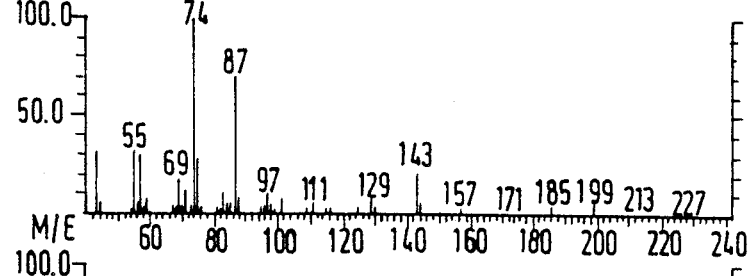
FIG.8d
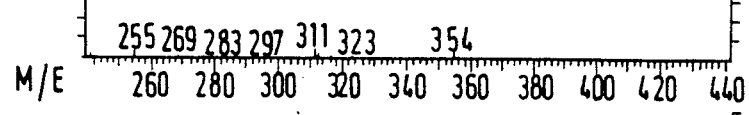
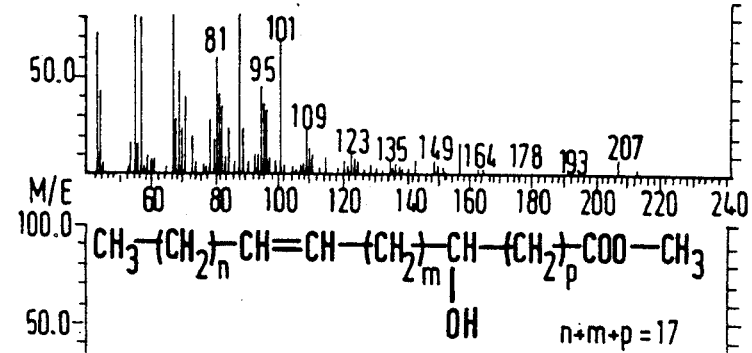
FIG.8e

SPHINGOPHOSPHOLIPIDS CONTAINING INOSITOL, THEIR PRODUCTION, AND THEIR APPLICATION AS INDUCERS OF RESISTANCE TO VARIOUS CRYPTOGAMIC DISEASES IN PLANTS

FIELD OF THE INVENTION

The present invention relates to new sphingophospholipids containing inositol, to methods by means of which they may be obtained, as well as to their application by way of inducers of resistance in plants capable of being infested by pathogenic fungi, in particular in cereals such as wheat and corn, Solanaceae such as capsicum, tomato and tobacco, and Cucurbitaceae such as melon, with respect to their natural parasites. These new sphingophospholipids according to the invention are also effective, in the absence of pathogenic fungi, to enhance the metabolism and physiology of the healthy plant.

The term "inducer of resistance" is understood to mean a substance synthesized by the fungus, participating in the host-parasite interaction and capable of inducing, in the plant, a state of resistance or of triggering phenomena associated with this resistance. Such substances are also designated by the term "elicitor", which had been introduced initially to describe substances capable of inducing the production of phytoalexins (antibiotic defence substances) in plants when they are attacked by a bacterium or a fungus.

Thus, the agricultural importance of isolating such eliciting agents is that their controlled application to plants leads the latter to defend themselves against their natural parasites, where appropriate through the intervention of phytoalexins.

BACKGROUND OF THE ART

Shortly after the isolation and characterization of the first phytoalexins, it was shown that mycelial extracts of *Monilia fructicola*, a fruit tree pathogen, contained a peptide, referred to as monilicolin A, capable of inducing the accumulation of phaseolin (phytoalexin) in the endocarp of the bean *Phaseolus vulgaris* [Cruickshank and Perrin, Life Sciences, 7, 449–458 (1968)]. Since this study, many eliciting preparations have been isolated, but they have essentially been partially purified fractions. In effect, the purification of elicitor molecules from crude fungal extracts is complicated by response curves that are multiphasic or variable according to the dose applied, the partial or total loss of activity, the response resulting from the interaction of different compounds present in the mixture, or quite simply the chemical nature of the elicitors.

In the *Phytophthora capsici*—Capsicum system, *Capsicum cotyledons*, kept alive on the fungal culture filtrate, exhibit a lower sensitivity with respect to this pathogen [Molot et al., Annales de Phytopathologie, 12, 95–107 (1980)]. An identical effect may be obtained using isolated fractions of culture filtrates or of the mycelium [Molot et al., Annales de Phytopathologie, 12, 379–387 (1980); Coulomb et al., Comptes Rendus de l'Académie des Sciences de Paris, series D, 290, 275–277 (1980)].

Molot et al. have observed that, in capsicum, the reaction is not accompanied by any accumulation of phytoalexin [Agronomie, 4, 829–833 (1984); Phytopathologische Zeitschrift, 112, 268–276 (1985)]. Other defence mechanisms must hence be envisaged.

BRIEF DESCRIPTION OF THE INVENTION

The analysis of the mycelial extracts of different strains of Phytophthora has enabled the Applicant to discover new elicitor molecules which are sphingophospholipids containing inositol, which have been obtained in the form of mixtures with one another (sphingophospholipid fractions) and which it has been possible to isolate in the pure state.

BRIEF DESCRIPTION OF THE DRAWINGS

FIG. 1. shows the relationship between the sensitivity of the *Capsium cotyledons* and the phospholipid concentration.

DETAILED DESCRIPTION OF THE INVENTION

Figure 1:
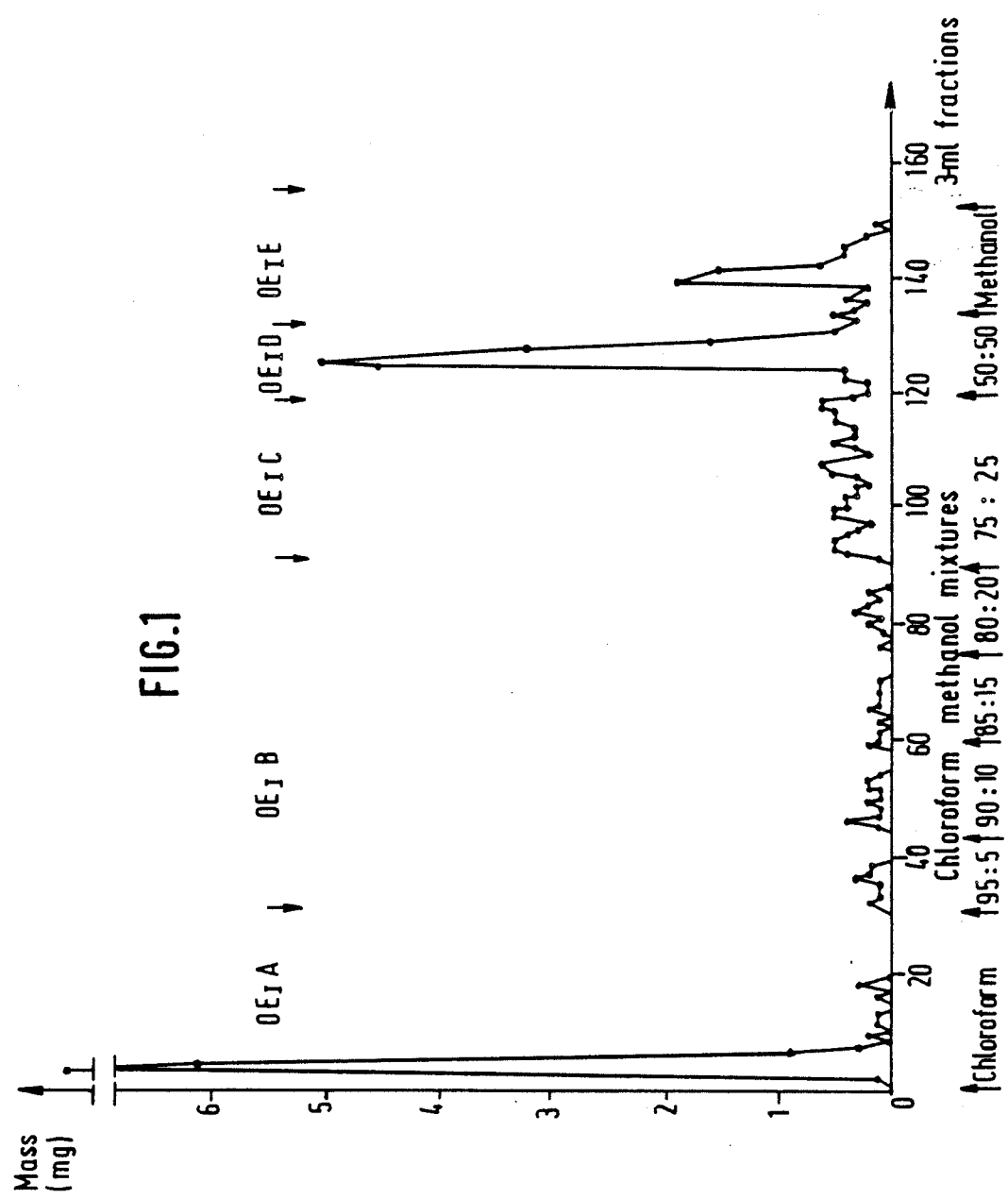
FIGS. 1 to 3 are elution curves on a column of Bio Sil HA silicic acid.

The subject of the present invention is hence, in the first place, the new sphingophospholipids containing inositol, represented by the general formula (I):

$$CH_3-(CH_2)_{\overline{10}}CH=CH-\underset{OH}{CH}-\underset{\underset{Z-C}{\overset{|}{NH}}}{CH}-CH_2-O-\underset{OH}{\overset{O}{\underset{\|}{P}}}-O-\text{inositol}$$

in which Z denotes the residues:

$$CH_3-(CH_2)_{17}-\underset{OH}{CH}-CH=CH-;$$

$$CH_3-(CH_2)_{19}-\underset{OH}{CH}-;$$

-continued

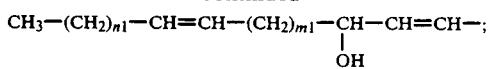

with $0 \leq n1 \leq 15$; $0 \leq m1 \leq 15$ and $n1+m1=15$; and
$CH_3-(CH_2)_{n2}-CH=CH-(CH_2)_{m2}-$, with $0 \leq n2 \leq 18$; $0 \leq m2 \leq 18$, and $n2+m2=18$.

The invention relates more especially to the new sphingophospholipid containing inositol of formula (Ia):

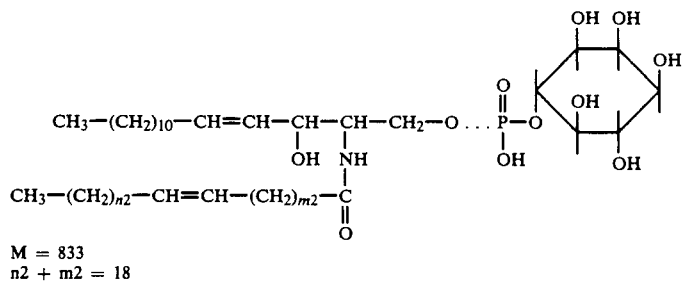

whose molecular mass is 849 daltons and which has proved to be very active.

The invention also relates to all sphingolipid fractions consisting of mixtures of at least two different compounds of formula (I), as defined above, and, as a specially preferred category, to sphingolipid fractions consisting of a major proportion of the compound of formula (Ia) and a minor proportion of at least one other compound of formula (I), as defined above, in other words at least one ceramide composed of $C_{16}$-sphingosine and of a fatty acid corresponding to a hydroxydocosanoic acid (M=851 d) or to a hydroxydocosadienoic acid (M=847 d) or to a docosenoic acid (M=833 d):

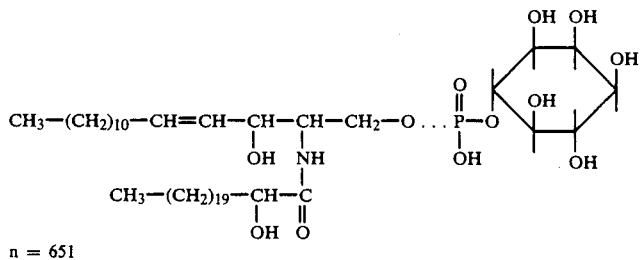

n = 651

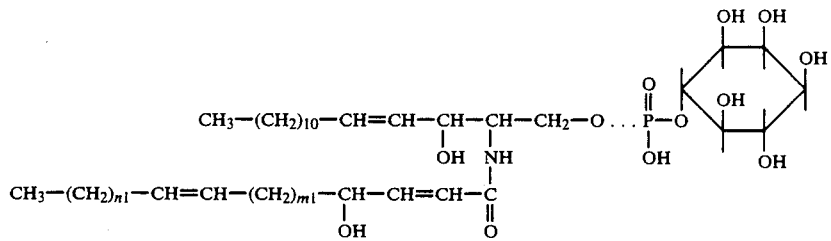

M = 847
n1 + m1 = 15

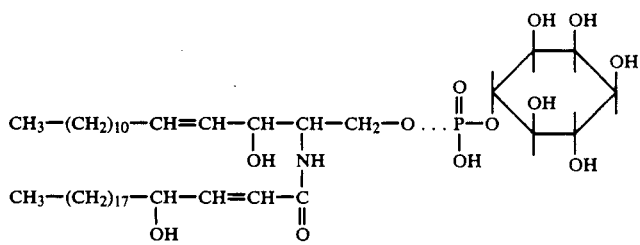

M = 833
n2 + m2 = 18

Sphingolipids containing inositol are quite widely represented in nature, especially in plants, yeasts, bacteria and fungi. However, few structures are known. In fungi, the long-chain base is generally represented by $C_{18}$-sphingosine or $C_{18}$-phytosphingosine; the most common fatty acids are $C_{26}$ acids hydroxylated at the 2-position [Lainé, Chemistry and Physics of Lipids, 42, 129–135 (1986)]. The sphingophospholipids containing inositol according to the present invention hence represent a new molecule as a result of the presence of $C_{16}$-sphingosine. The preferred compound, of formula (Ia), is also novel as a result of the existence of a 4-hydroxy acid.

The subject of the present invention is also a method for preparing the sphingolipid fractions as defined above and the compounds of general formula (I) as defined above, in which method:

in a first stage, a mycelial extract of Phytophthora is prepared, the said extract showing a resistance-inducing activity in a plant capable of being infested by a pathogen belonging to the species Phytophora;

in a second stage, an extraction of the total lipids of the said mycelial extract is carried out; and in a third stage, a fractionation of these lipids is carried out by adsorption chromatography on silicic acid, in order to collect the fractions retaining the major part of the initial activity, additional purifications leading to the production of the desired compound of formula (I).

Generally speaking, the sphingolipid fractions as defined above and the compounds of general formula (I) as defined above may be prepared by extracting the mycelial lipids of Phytophthora to obtain the said fractions, additional purifications leading to the production of the desired compound of formula (I).

The sphingolipid fractions as defined above and the compounds of general formula (I) as defined above may also be prepared in the following manner:

in a first stage, grinding of the mycelium of Phytophthora is carried out and the suspension is filtered to collect, on the one hand the crude mycelial walls, and on the other hand a mycelial filtrate, which constitute desired fractions; and in a second stage, extraction of the wall lipids is carried out, these lipids also constituting desired fractions, additional purifications of the above mentioned fractions leading to the production of the desired compound of formula (I).

The purifications of the sphingolipid fractions are advantageously performed by adsorption chromatography on silicic acid.

In all the methods mentioned above, mycelium of *Phytophthora capsici* or of *Phytophthora parasitica* is advantageously used as starting material.

The invention also relates to the application of the compounds of formula (I) as defined above and the sphingolipid fractions as defined above, by way of agents inducing resistance to cryptogamic diseases in plants capable of being infested by a pathogenic fungus, in particular for the purpose of protecting cereals and plants belonging to the Solanaceae and Cucurbitaceae families.

Thus, there may be mentioned, by way of example, the protection of wheat with respect to cryptogamic diseases of the aerial part, provoked for example by *Septoria nodorum* and *Erysiphe graminis*, and of diseases provoked by root fungi such as *Gaemannomyces graminis*; of capsicum with respect to *Phytophthora capsici*; of melon with respect to *Pseudoperonospora cubensis*; of tomato with respect to *Phytophthora infestans*; and of "Xanthi" tobacco with respect to *Phytophthora parasitica* var. *nicotianae*. The effective protection of major crop plants, such as wheat, that can be obtained with the compounds and sphingolipid fractions of the invention is of very great importance.

Another advantage of the elicitors according to the present invention is the systemic nature of the protection. In other words, the application of the elicitor on a particular part of the plant (its foliage, for example) leads to a total protection of the latter, both of its aerial system and of its root system. Furthermore, the plant which is treated with the sphingophospholipids according to the invention is protected during all its life. In the same way, the treatment of the seed protects the plant during all its life.

Yet another advantage of the elicitors of the invention is that they exert a physiological effect on the heatly plant material, manifesting itself, in particular, in an improvement of the vegetative state, an earlier maturation, a rise in the chlorophyll content and a modified size, for a better grain yield, for example.

The present invention hence also relates to an eliciting composition, which contains, as active ingredient, at least one compound of formula (I), as defined above, or at least one spingolipid fraction, as defined above, in a medium acceptable in agriculture.

Thus, the composition according to the invention is advantageously present in a form suitable for spraying on the aerial system of a plant, or for dipping a seed of the said plant in the said composition, or alternatively for coating the said seed in the wet state with the said composition, the concentration of the latter being, in particular, from about 1 to 25 $\mu$g/ml in the case of the treatment of the aerial system of the plant, and from about 1 to 10 $\mu$g/ml in the case of a treatment by dipping or coating of the seed. Since the compounds of formula (I) are, for the most part, insoluble in water, they are generally made into a milky suspension by passage through a homogenized (Ultra-Turrax).

The subject of the present invention is finally a method for treating a plant, in particular for protecting this plant with respect to a pathogenic fungus or several pathogenic fungi by inducing in it resistance to these fungi, or, in the absence of pathogenic fungus or fungi, for enhancing the metabolism and physiology of the healthy plant, wherein an eliciting composition as defined above is applied by spraying on the aerial system of the plant.

In the case of wheat, a spraying is performed on the wheat at the end of tillering and/or the beginning of bolting.

The invention also relates to a method for treating a plant, in particular for protecting this plant with respect to a pathogenic fungus or several pathogenic fungi by inducing in it resistance to these fungi, or, in the absence of pathogenic fungus or fungi, for enhancing the metabolism and physiology of the healthy plant, wherein the seed of the said plant is left to swell for a period of time between 24 and 48 hours in an eliciting composition as defined above (complete impregnation of the seed), or alternatively a coating of the integument is carried out by the wet method, by mixing the said seed with the said eliciting composition.

A detailed description will now be given of the isolation of the sphingophospholipids containing inositol of the present invention from the mycelium of *Phytophthora capsici* and the characterization of these new substances (example 1), and two other methods of obtaining sphingophospholipids of the invention (examples 2 and 3), as well as their resistance-inducing activity in certain plants, by way of examples (examples 4 and 5).

EXAMPLE 1

A. Isolation and Purification of the Eliciting Phospholipids according to the Invention in the Mycelium of *Phytophthora capsici*

First Stage: Isolation of a Mycelial Extract of *Phytophthora capsici*

The starting mycelium is derived from a *Phytophthora capsici* culture performed on Messiaen-Lafon synthetic medium [Molot et al., Annales de Phytopathologie, 12, 95-107 and 379-387 (1980)].

This mycelial extract (ME) is prepared according to the following protocol:

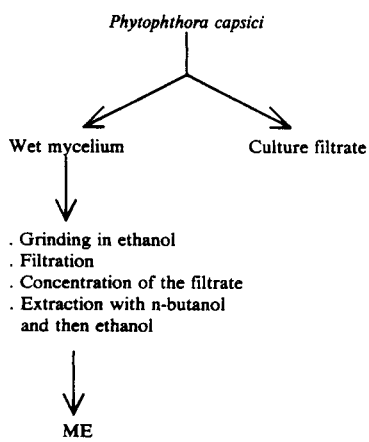

The wet mycelium is ground in eight volumes of 95% strength ethanol. After filtration, an alcoholic extract is obtained, which is concentrated to dryness and then taken up with water. This new preparation is extracted successively three times with n-butanol and then once with absolute alcohol. The fraction insoluble in alcohol is taken up with water and then lyophilized. It represents the mycelial extract ME.

Second Stage: Extraction of the Total Lipids Present in the Mycelial Extract (ME) according to the Method of Folch [Journal of Biological Chemistry, 226, 497-509 (1957)]

The mycelial extract (ME) prepared in the preceding stage is suspended in a chloroform/methanol/water (40:20:15; v/v/v) mixture, in a (1:300; g/ml) ratio. After agitation for 48 hours at room temperature, and allowing settling to occur, the lipid compounds are separated from the water-soluble and glycoconjugate fractions which are solubilized in the upper phase of the solvent.

Third Stage: Fractionation of the Lipids by Two Successive Adsorption Chromatographic Runs (a) Chromatography on a Column of *Mallinckrodt silicic Acid*/Celite 545 (3:1; m/m)

The organic extract (OE) obtained in the preceding stage is fractionated by adsorption chromatography on a column of Mallinckrodt silicic acid (152 μm-100 mesh), activated for 15 hours at 100° C., mixed with Celite 545 in a (3:1; m/m) ratio.

Three fractions are collected, eluted with chloroform ($OE_I$), 25% methanol in chloroform ($OE_{II}$) and pure methanol ($OE_{III}$).

(b) Chromatography on a Column of Silicic Acid (Bio Sil HA)

The fractions $OE_I$, $OE_{II}$ and $OE_{III}$ are each deposited, in solution in chloroform, on a column of Bio Sil HA silicic acid (45 μm-325 mesh) (1.8×46 cm), activated for 15 hours at 100° C.

In all three cases, the elution is carried out with chloroform and then with increasing contents of methanol in chloroform: 5, 10, 15, 20, 25, 50 and 100% of methanol.

Figure 2:
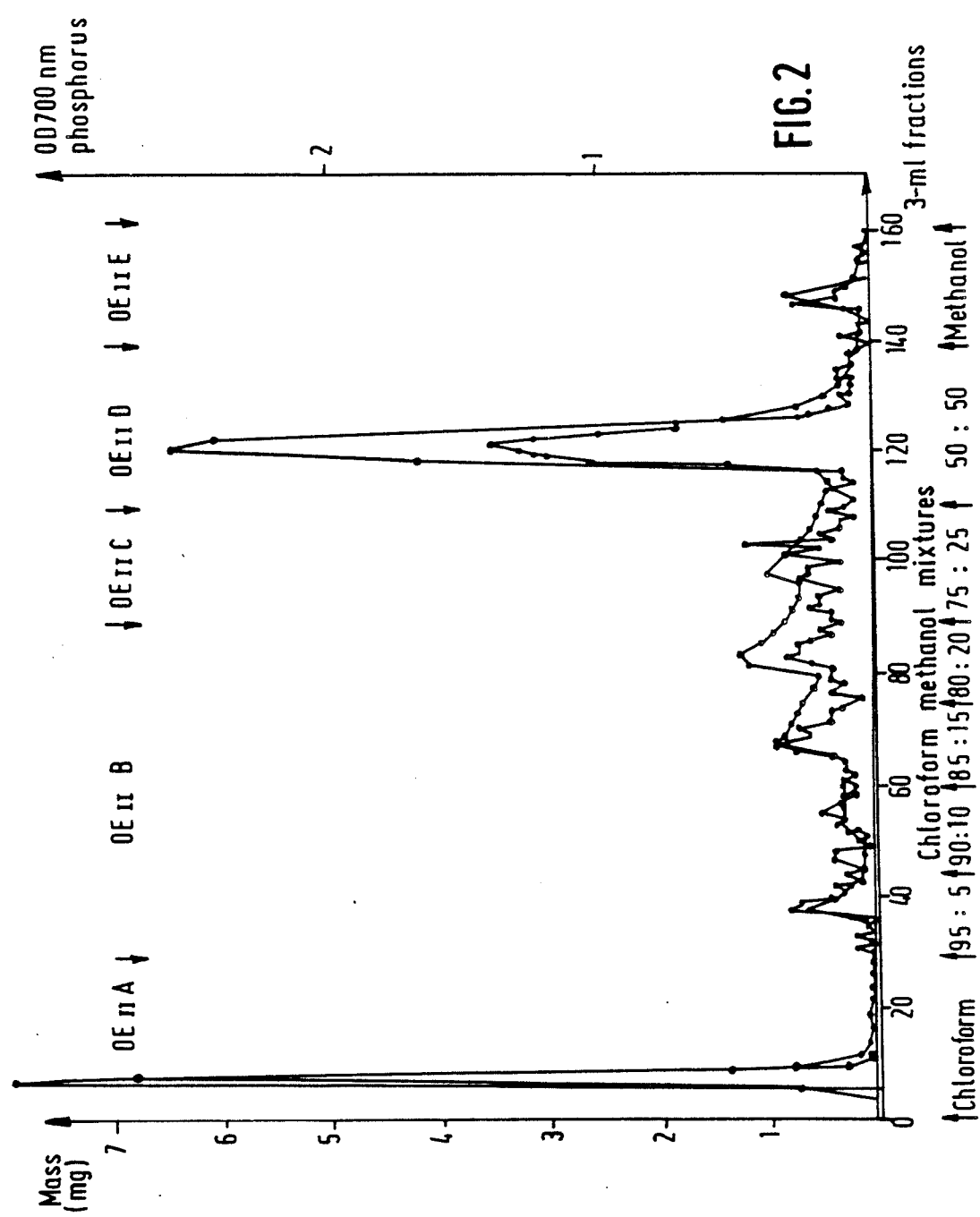
Figure 3:
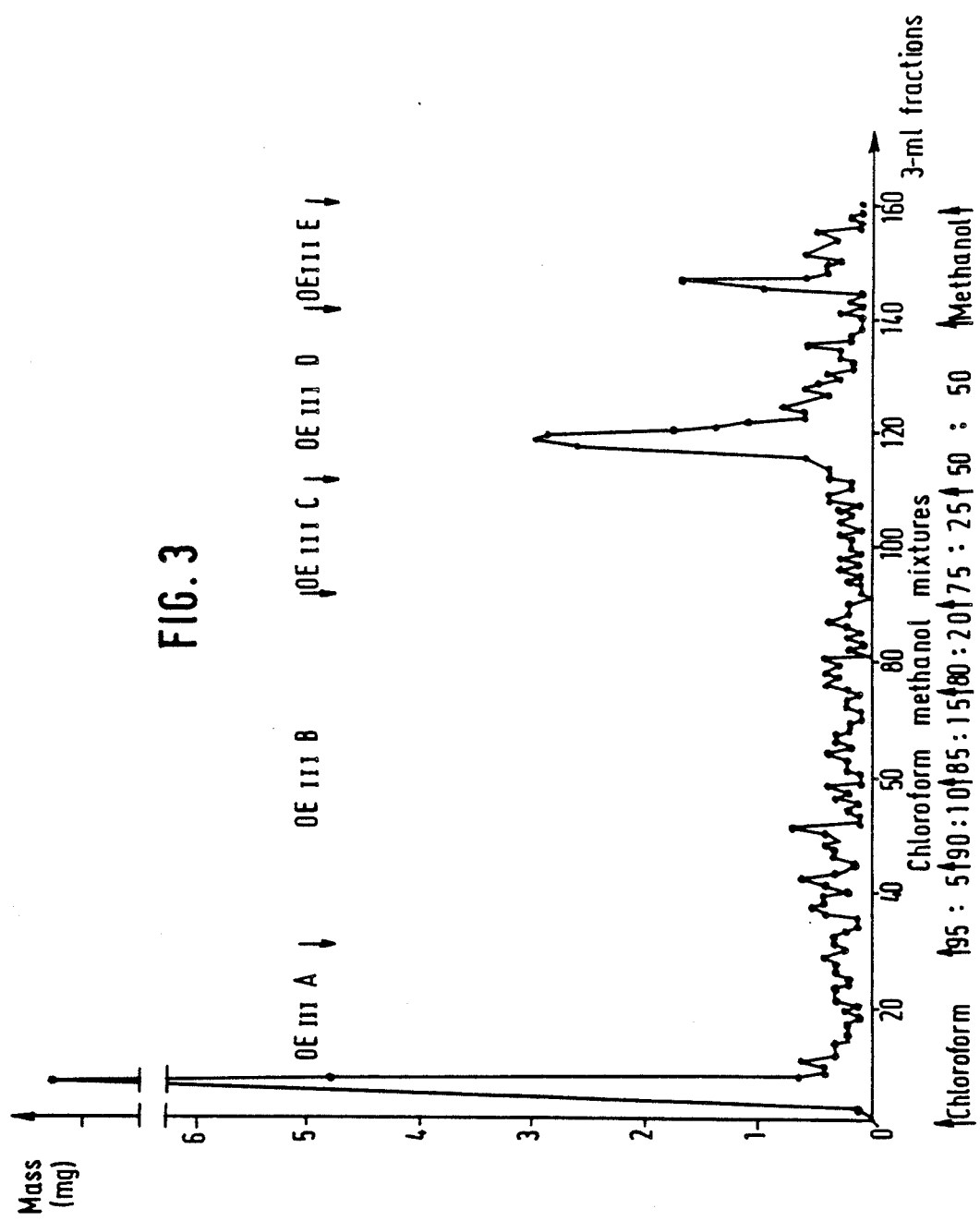

FIGS. 1 to 3 show the elution curves in terms of mass which are obtained by fractionation by chromatography of the fractions $OE_I$, $OE_{II}$ and $OE_{III}$, respectively, on a column of Bio Sil HA silicic acid.

In addition, the eluate of the fraction $OE_{II}$ is followed by a phosphorus assay according to the method of Lowry et al., [Journal of Biological Chemistry, 207, 1-17 (1965)] (FIG. 2).

In all three cases, the fraction retaining the bulk of the initial eliciting activity is eluted by 50% methanol in chloroform. These are the fractions $OE_ID$, $OE_{II}D$ and $OE_{III}D$.

Fourth Stage: Analysis of the Different Fractions by Thin Layer Chromatography (HPTLC)

(1) Analysis by One-Dimensional HPTLC

The lipid fractions $OE_I$, $OE_{II}$ (A, B, C, D, E) and $OE_{III}$ (A, B, C, D, E), separated by chromatography on Bio Sil HA silicic acid, are analyzed in the presence of controls on Merck 5628 silica gel 60 plates (100×100×0.2 mm). The chromatograph is developed in Heape's solvent [Journal of Chromatography, 322, 391-395 (1985)], and the plates are visualized with the phosphomolybdic reagent of Dittmer and Lester [Journal of Lipid Research, 5, 126-127 (1964)], modified by Vaskovsky and Kostetsky [Journal of Lipid Research 9, 936 (1968)]. The results of this quantitative analysis are depicted in the following table 1:

TABLE 1

Analysis by HPTLC of the composition of phosphorylated complex lipids in the fractions eluted on Bio Sil HA silicic acid

| Fraction | | Rf of the spots referred to Ptd Ins | | | |
|---|---|---|---|---|---|
| $OE_I$ | D | | 0.76 | | |
| $OE_{II}$ | A | 0.1 | 0.76 | | |
| | B | 0.1 | 0.76 | 1.05 | |
| | C | 0.1 | 0.76 | | 1.38 |
| | D | | 0.76 | | |
| | E | 0.1 | | | |
| $OE_{III}$ | A | 0.1 | | | |
| | B | 0.1 | 0.76 | | |
| | C | 0.1 | 0.76 | | |
| | D | 0.1 | 0.76 | | |
| | E | 0.1 | | | |
| Phosphatidylcholine | | 0.33 | | | |
| Sphingomyelin | | | 0.40 | | |
| Phosphatidylserine | | | | 0.90 | |
| Phosphatidylinositol | | | | | 1.00 |
| Phosphatidic acid | | | | | 1.33 |
| Phosphatidyl-glycerol | | | | | 1.40 |
| Phosphatidylethanol-amine | | | | | 1.57 |

The fractions A, B, C and E present in $OE_{II}$ and $OE_{III}$ give several spots. They correspond to mixtures of phospholipids; only the active fractions $OE_ID$ and $OE_{II}D$ give a single spot of Rf/Ptd Ins 0.76, different from that of the control phospholipids. The results of an analysis of the compounds $OE_ID$ and $OE_{II}D$ by thin layer chromatography are summarized in Table 2:

TABLE 2

Analysis of the compounds $OE_ID$ and $OE_{II}D$ by one-dimensional HPTLC

| Compound | | Rf/Ptd Ins | Phospholipids | | Choline DRAGEN-DORF | Visualization methods | | | Primary amines (NINHYDRIN |
|---|---|---|---|---|---|---|---|---|---|
| | | | | | | Lipids | | | |
| | | | DITTMER VASKOVSKY | FEWSTER | | IODINE | VANILLIN | RHODAMINE + FLUORESCEIN | |
| $OE_ID$, | $OE_{II}D$ | 0.76 | + | + | − | + | + | + | − |
| Ptd | Cro | 1.40 | + | + | − | + | + | + | − |
| Ptd | Cho | 0.33 | + | + | + | + | + | + | − |
| Ptd | Ser | 0.80 | + | + | − | + | + | + | + |
| Ptd | Etn | 1.57 | + | + | − | + | + | + | + |
| Phosphatidic Ac. | | 1.33 | + | + | − | + | + | + | − |
| Sphingomyelin | | 0.40 | + | + | + | + | + | + | − |
| Ptd | Ins | 1.00 | + | + | − | + | + | + | − |
| Ptd Ins 4 P | | . | + | + | − | + | + | + | − |
| Ptd Ins 4.5 PP | | . | + | + | − | + | + | + | − |
| Cardiolipin | | . | + | + | − | + | + | + | − |
| Tripalnitin | | 3.00[a] | − | − | − | + | +/− | + | − |
| Fatty acids | | 3.00[a] | − | − | − | + | +/− | + | − |
| Tridecylamine | | 1.31 | − | − | − | + | + | + | + |

NB the Rf values referred to phosphatidylinositol are given for a migration on a silica gel plate (Merck art. 5628) in solvent of Heape et al.
[a]Solvent front These results show that $OE_ID$ and $OE_{II}D$ are visualized with specific reagents for lipids (iodine, sulfuric vanillin, rhodamine and fluoracine) and for phospholipids (Dittmer-Vaskovsky and Fewster), but are not demonstrated either with the visualizing agent for primary amines (Russel's ninhydrin) or with the visualizing agent for tertiary amines (Dragendorf's reagent), thereby confirming that the expected phospholipid is different from phosphatidylethanolamine and phosphatidylserine, and that it does not contain choline.

(2) Analysis of the Compounds $OE_ID$ and $OE_{II}D$ by Two-Dimensional HPTLC

The fractions $OE_ID$ and $OE_{II}D$ are chromatographed on a thin layer of silica gel (Merck 5628) in two systems, one described by Owens [Biochemical Journal, 100, 354–361 (1966)] and the other described by Rouser & al. [Lipid Chromatographic Analysis, vol. 1, G. W. Marinetti ed. E. Arnold Ltd., London, pages 99–162 (1967)]. The results of this two-dimensional analysis are recorded in Table 3.

TABLE 3

Analysis of the phospholipid isolated from *Phytophthora capsici* by two-dimensional HPTLC

| Compound | Rf referred to phosphatidylinositol | |
|---|---|---|
| | Rouser's solvent | Owens's solvent |
| Phosphatidic acid (PA) | (0.4; 4.6) | (1.6; 1.2) |
| Phosphatidylinositol (PI) | (1.0; 1.0) | (1.0; 1.0) |
| Phosphatidylglycerol (PG) | (4.0; 2.2) | (1.6; 1.2) |
| Phosphatidylcholine (PC) | (2.6; 1.3) | (0.4; 1.0) |
| Phosphatidylserine (PS) | (1.1; 1.4) | (0.5; 1.1) |
| Phosphatidylethanolamine (PE) | (3.5; 2.2) | (1.5; 1.4) |
| Cardiolipin (CL) | (4.6; 3.0) | (1.6; 1.4) |
| Sphingomyelin (SPM) | (1.4; 1.1) | (0.2; 0.9) |
| $OE_ID$ and $OE_{II}D$ | (0.9; 0.7) | (0.8; 1.1) |

Owens's solvent: D1 Chloroform/Methanol/Water/Acetic acid (65:43:3:1); D2 Chloroform/Methanol/Water (60:35:1)
Rouser's solvent: D1 Chloroform/Methanol/28% strength aqueous ammonia (65:35:5) D2 Chloroform/Acetone/Methanol/Acetic acid/Water (10:4:2:2:1)
Visualizing agent of Dittmer and Lester modified by Vaskovsky and Kostetsky In the solvent of Kunz and Kozin [Clinica Chimica Acta, 27, 185–196 (1970); Biochimica et Biophysica Acta, 296, 331–334 (1973)], $OE_ID$ and $OE_{II}D$ give a single spot of Rf (0.27; 0).

In each of the solvents, the compounds $OE_ID$ and $OE_{II}D$ give a single spot different from all the control phospholipids deposited as a reference. These compounds represent the desired eliciting phospholipid isolated from *Phytophthora capsici*.

B-COMPOSITIONAL ANALYSIS OF THE PHOSPHOLIPID OF THE INVENTION (1) Analysis of the Non-Lipid Constituents The phospholipid is hydrolyzed at 100° C. with N or 6N hydrochloric acid overnight. After reduction with sodium borohydride overnight at room temperature and acetylation for 20 minutes at 100° C. with a pyridine/acetic anhydride (1:1; v/v) mixture, the hydrolyzates are analyzed by gas chromatography. The presence is noted of a single peak, whose retention time is identical to that of control inositol acetate. No neutral or aminated monosaccharide is identified. Glycerol is also absent.

Figure 4:
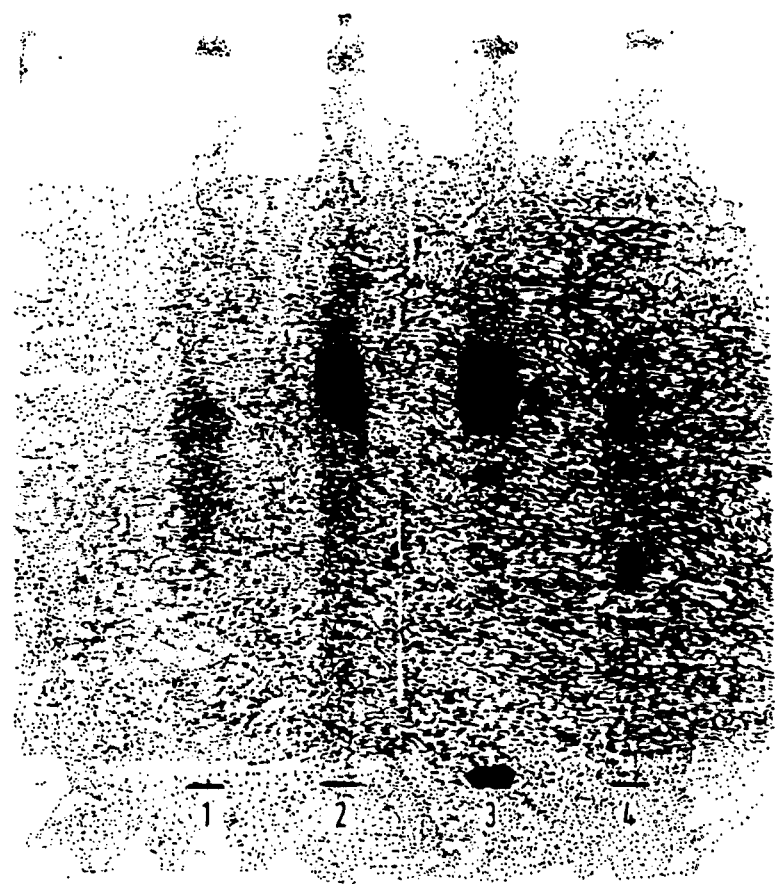
FIG. 4 is a non-lipid analysis on silica gel 60.

A methanolysis with 2N methanolic hydrochloric acid at 80° C. for 5 hours enables an amino compound to be isolated. The reaction medium is extracted with chloroform after alkalinization. Chloroform extract is analyzed by HPTLC on silica gel 60 (Merck art. 5628) in the solvent of Heape et al. FIG. 4 shows the results obtained.

Legend to FIG. 4

1. $C_{18}$ sphingosine (Sigma S 6136)
2. Amino compound isolated from the phospholipid of *Phytophthora capsici*
3. Sphingosine isolated from sphingomyelin (Sigma S 7004)
4. $C_{18}$ sphingosine sulphate (Sigma S 3263).

The presence of a spot whose Rf is close to that of control sphingosine is observed (Table 4).

TABLE 4

Rf values of the long-chain bases can be visualized with ninhydrin in HPTLC on silica gel 60 in the solvent of Heape et al.

| Compound | Rf referred to $C_{18}$-sphingosine | |
|---|---|---|
| $C_{18}$-Sphingosine (1) | . | 1 | . |
| $C_{18}$-Sphingosine sulphate (4) | . | 1 | . |
| Amino compound derived from sphingomyelin | 0.5 | . | 1.14 |
| Amino compound derived from the phospholipid of | . | . | 1.14 |

TABLE 4-continued

Rf values of the long-chain bases can be visualized with ninhydrin in HPTLC on silica gel 60 in the solvent of Heape et al.

| Compound | Rf referred to $C_{18}$-sphingosine |
|---|---|
| *Phytoohthora capsici* | |

This amino compound is identified by mass spectrometry of the N-acetyl and O-trimethylsilyl derivative according to the method described by Lainé et al [Methods in Membrane Biology, Vol. 2, E. D. Korn ed., Plenum Press, pages 205-244 (1974)]. The hydrolyzate is treated with methanol/acetic anhydride (4:1; v/v) mixture at 20° C. for 15 hours, and then with TMSi-S Universal Reagent (Serva) at 60° C. for 30 minutes.

Figure 5:
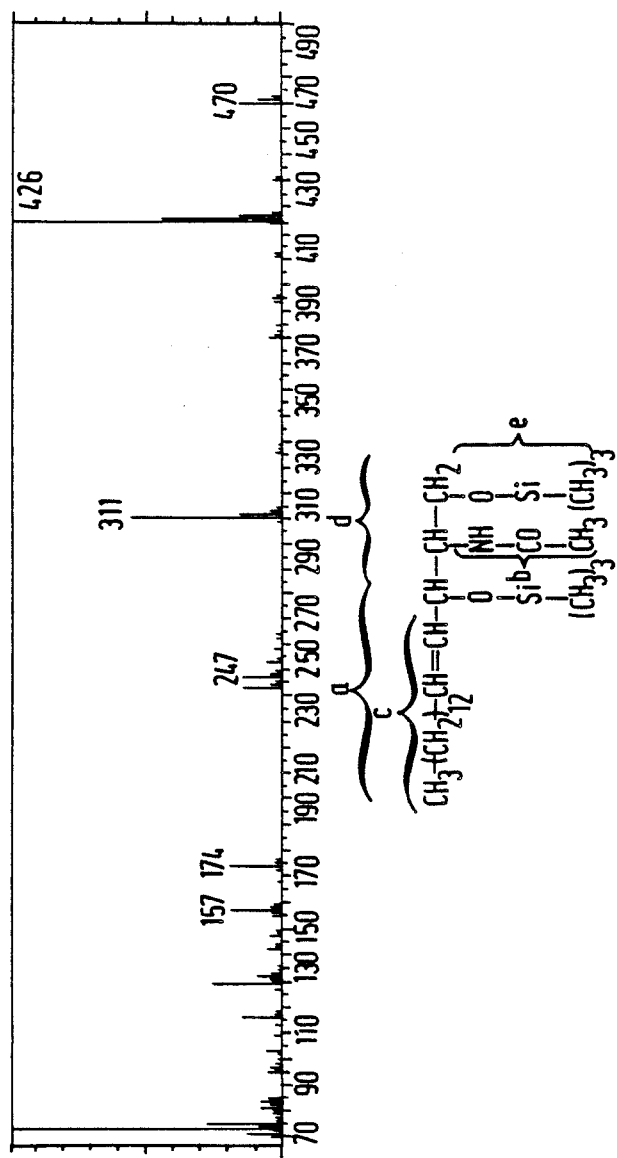
FIG. 5 is a mass spectrum showing fragmentations characteristic of sphingoid derivatives.
Figure 6:
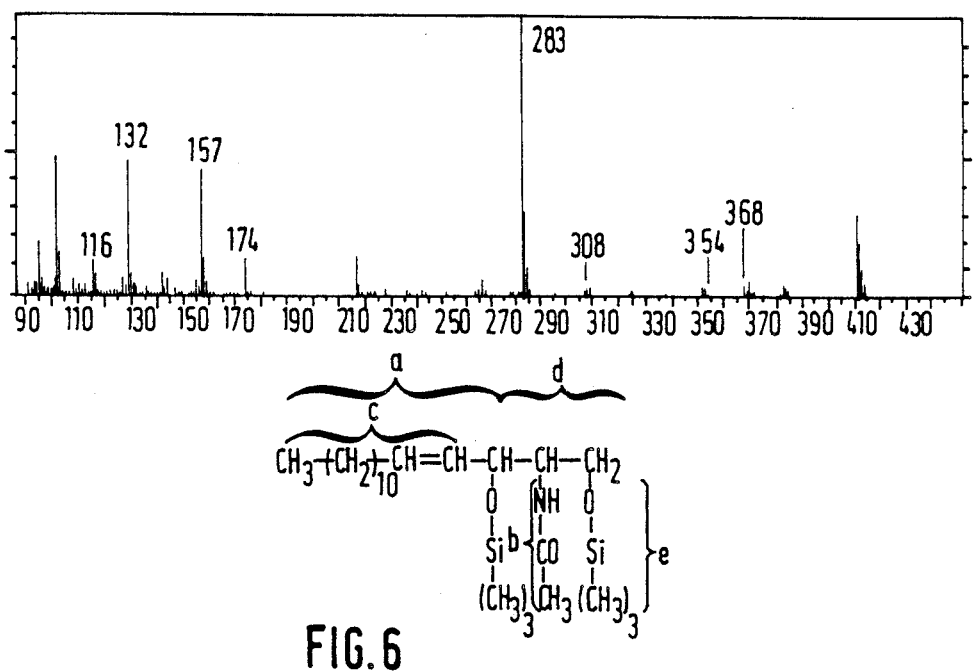
FIG. 6 is the spectrum obtained with $C_{18}$-sphingosine.

The reaction medium is analysed by gas chromatography coupled with mass spectrometry. The mass spectrum shown in FIG. 5 shows the fragmentations characteristic of sphingoid derivatives proposed by Gaver and Sweeley [Journal of the American Chemical Society, 88, 3643-3647 (1966)] and by Hammarström [Journal of Lipid Research, 11, 175-182 (1970)] and observed in the spectrum obtained with $C_{18}$-sphingosine (FIG. 6, Table 5).

TABLE 5

Interpretation of the electron impact spectra of control $C_{18}$-sphingosine and of the long-chain base (LCB) of the phospholipid of the invention, the latter compound being O-trimethylsilylated and N-acetylated.

| Characteristic fragments | LCB of PX m/z | $C_{18}$-Sphingosine m/z |
|---|---|---|
| M - $CH_3$ | — | 470 |
| M — (b + 1) | — | 426 |
| M — e | 368 | — |
| M — (($CH_3$)$_3$Si—OH) | — | 395 |
| M — ($CH_2$=$O^+$—Si($CH_3$)$_3$) | 354 | 382 |
| M — (($CH_3$)$_3$Si—OH) — $CH_3$ | 352 | 380 |
| M — (b + 1) — ((CH) Si—OH) | 308 | 336 |
| M — d | 283 | 311 |
| M — ($CH_2O^+$—Si($CH_3$)$_3$) — (($CH_3$)$_3$Si—OH) | 264 | 292 |
| M — (c — (($CH_3$)$_3$Si)) | — | 247 |
| M — (a — (($CH_3$)$_3$Si)) | 176 | 176 |
| M — ((a + 1) — (($CH_3$)$_3$Si)) | 175 | 175 |
| M — c | 174 | 174 |
| M — (c — (($CH_3$)$_3$Si)) — (($CH_3$)$_3$Si—OH) | 157 | 157 |
| ($CH_3$)$_2$Si=$O^+$—Si($CH_3$)$_3$ | 147 | 147 |
| b + 1 + (($CH_3$)$_3$Si) | 132 | 132 |
| M — (b + c) | 116 | 116 |
| M — (b + 1 + c) | 115 | 115 |
| CH=$O^+$—Si($CH_3$)$_3$ | 103 | 103 |
| $HO^+$—Si($CH_3$)$_2$ | nd | 75 |
| $^+$Si($CH_3$)$_3$ | nd | 73 |

The molecular peak is absent. Cleavage of the molecule between carbons 2 and 3 gives a peak of high intensity at m/z=283, corresponding to the fragment:

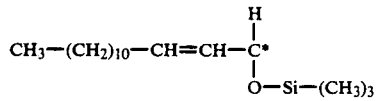

which enables the nature of the main chain to be defined. A peak of lower intensity is also observed at m/z=174, corresponding to the ion (CH(NH—CO—$CH_3$)—$CH_2$—O—Si($CH_3$)$_3$)$^+$, originating from this same fragmentation. The amino derivative present in the phospholipid being studied hence corresponds to $C_{16}$-sphingosine (FIG. 5, Table 5).

(2) Analysis of the Fatty Acids

The fatty acids are obtained after extraction of the acid hydrolyzate of the phospholipid with ether. They represent 32% of the phospholipid. They are methylated with diazomethane and analyzed in the form of methyl esters. The fatty acids are also liberated in the form of methyl esters after methanolysis of the phospholipid.

Figure 7:
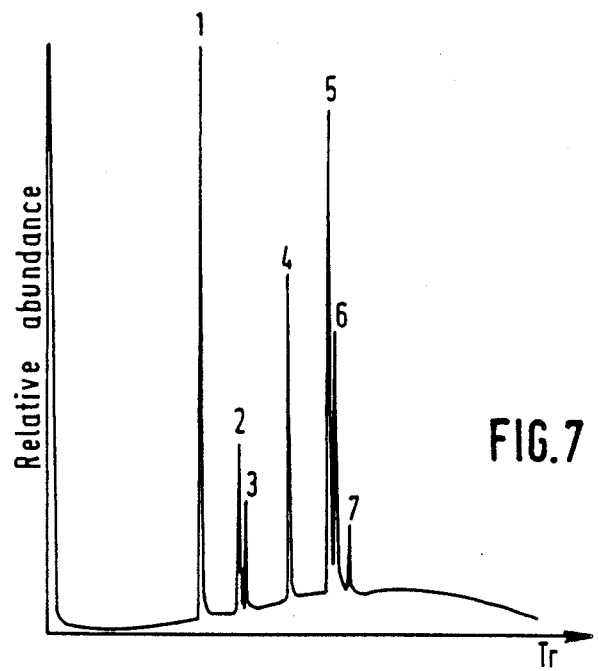
FIG. 7 is the chromatogram obtained from the methyl esters.
Figure 8A:
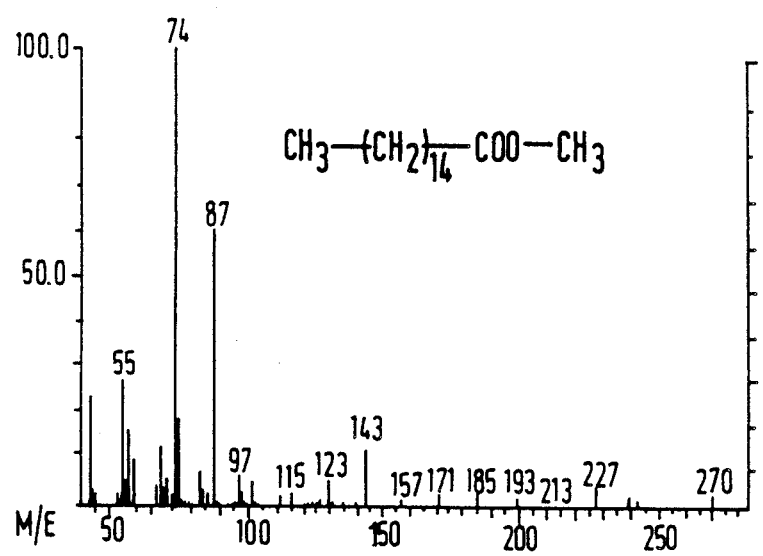
FIG. 8 shows the mass spectra of the methyl esters of hexadecanoic (a), eicosanoic (b), docosenoic (c), docosanoic (d) and hydroxydocosenoic (e) acids.
Figure 8B:
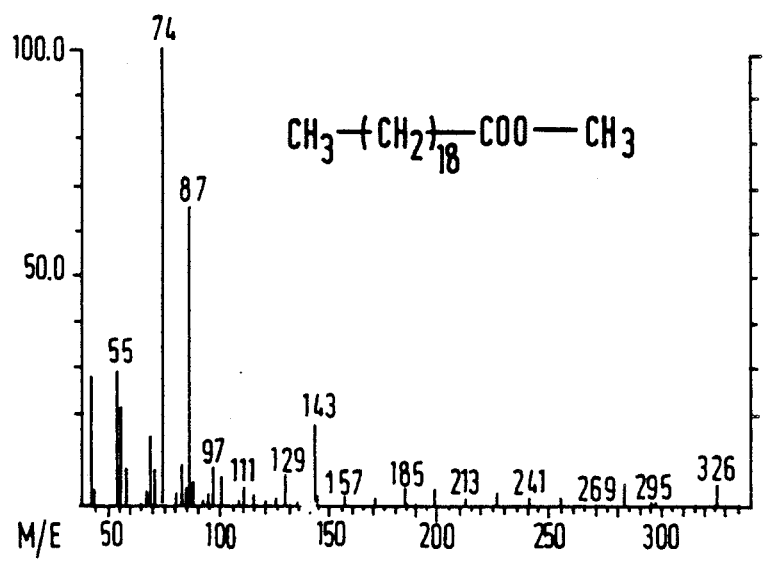

The methyl esters are then analysed by gas chromatography coupled with mass spectrometry. FIG. 7 shows the chromatogram obtained. The mass spectra are shown in FIG. 8.

Legend to FIG. 8

Mass spectra of the methyl esters of hexadecanoic (a), eicosanoic (b), docosenoic (c), docosanoic (d) and hydroxydocosenoic (e) acids, present in the phospholipid isolated from the mycelium of *Phytophthora capsici*.

The presence of the molecular peak is observed at m/z=270 (FIG. 8a), m/z=326 (FIG. 8b) m/z=352 (FIG. 8c), m/z=354 (FIG. 8d) and m/z=368 (FIG. 8e), corresponding, respectively, to the above mentioned methyl esters. The characteristic peaks corresponding to the fragment

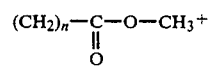

with n=1, m/z=74 and n=2, m/z=87, are present in the spectra (a), (b), (c) and (d). They are absent in the spectra corresponding to hydroxydocosenoic acid (FIG. 8e). In the latter, the peak is observed at m/z=350, originating from the departure of a molecule of water. Table 6 gives the nature and percentage of fatty acids identified in the phospholipid:

TABLE 6

Fatty acid composition of the phospholipid isolated from the mycelium of *Phytophthora capsici*

| Fatty acids identified | Mol % | Peak No. |
|---|---|---|
| Hexadecanoic acid | 26.2 | 1 |
| Octadecenoic acid | 5.7 | 2 |
| Octadecanoic acid | 2.8 | 3 |
| Eicosanoic acid | 11.6 | 4 |
| Docosenoic acid | 33.2 | 5 |
| Docosanoic acid | 16.1 | 6 |
| Hydroxydocosenoic acid | 4.3 | 7 |

Analysis by gas chromatography of the unhydrolyzed methylated phospholipid shows that 16% of palmitic acid is mixed with the latter.

(3) Analysis of the Phospholipid by FAB Mass Spectrometry and Elemental Microanalysis The phospholipid isolated from the mycelial extract of *Phytophthora capsici* was analysed by Fast Atom Bombardment. The mass spectra were produced on glycerol and thioglycerol matrices, in the positive and negative mode, before and after methanolysis.

Figure 9:
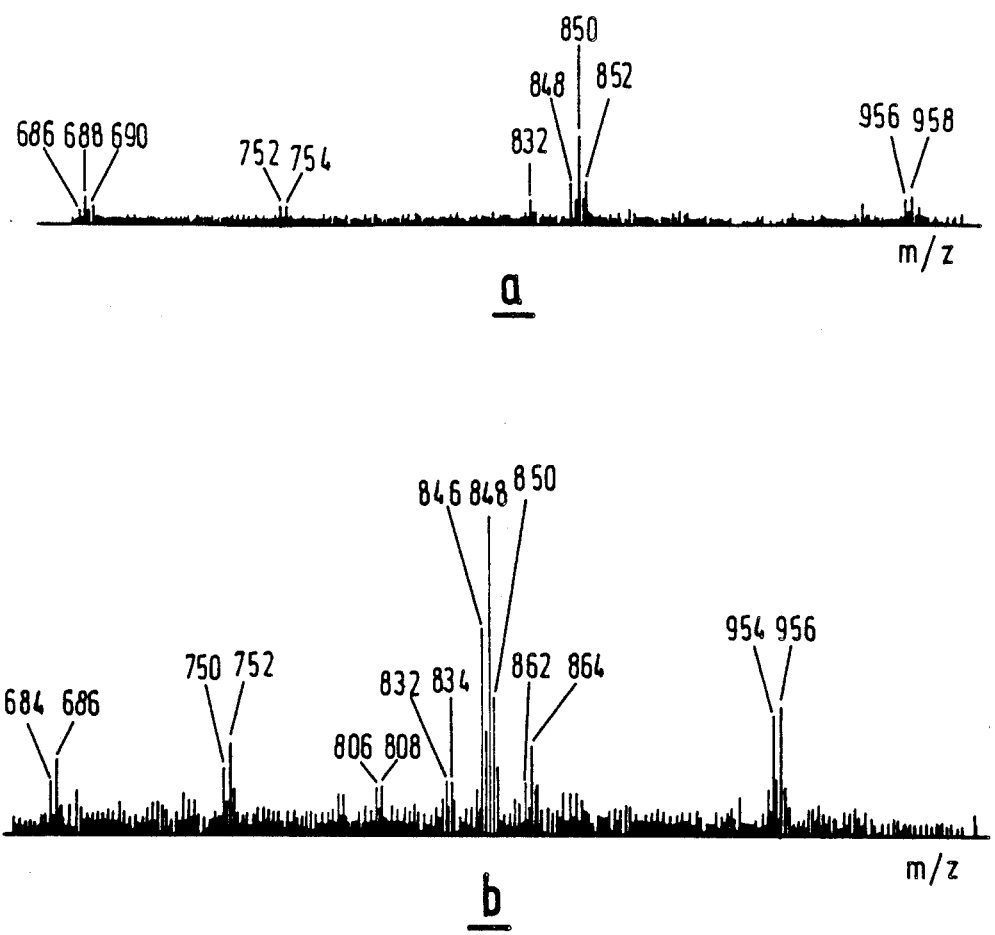
FIG. 9 shows the mass spectra of the phospholipid with FAB
(a) Positive FAB
(b) Negative FAB FIG. 10 summarizes the different stages of degradation of the phospholipid.

The mass spectrum of the native compound gives the molecular peak m/z=849 (FIG. 9).

Legend to FIG. 9

Mass spectra of the phospholipid isolated from *Phytophthora capsici* with FAB
(a) Positive FAB
(b) Negative FAB Table 7 gives the results of the fragmentations:

TABLE 7

Analysis of the phospholipid isolated from *Phytophthora capsici* by FAB spectrometry. Identification of the characteristic peaks.

| | Positive FAB | | | * |
|---|---|---|---|---|
| $(M + H + thioglycerol)^+$ | $(M + Na)^+$ | $(M + H)^+$ | $(M + H - 162)^+$ | |
| m/z | — | — | 852 | 890 |
| | 958 | 872 | 850 | 688 |
| | 956 | — | 843 | 686 |
| | — | — | 832 | — |
| | — | 776 | 754 | 592 |
| | — | — | 752 | 590 |

| | Negative FAB | | | * |
|---|---|---|---|---|
| $(M - H + (thioglycerol)2)^-$ | $(M - H + 16)^-$ | | | |
| | $(M - H + thioglycerol)^-$ | $(M - H)^-$ | $(M - H - 162)^-$ | |
| m/z | — | — | 850 | 688 |
| | 1064 | 956 | 864 | 843 | 686 |
| | 1062 | 954 | 862 | 846 | 684 |
| | — | — | 850 | 834 | — |
| | — | — | 848 | 832 | — |
| | — | — | — | 808 | — |
| | — | — | — | 806 | — |
| | 860 | 968 | — | 752 | — |
| | — | — | — | 750 | — |

*Departure of one molecule of inositol: −162

The presence is also observed of peaks of lower intensity corresponding to phospholipids mixed with the phospholipid being studied. The peak at m/z=688 in the positive FAB mass spectrum and m/z=686 in the negative FAB mass spectrum corresponds to the departure of one molecule of inositol, thereby demonstrating the presence of a single molecule of this constituent in the phospholipid being studied and its terminal position in the phospholipid.

The results of the elemental microanalysis, relating to the composition of the phospholipid being studied with respect to carbon, hydrogen, oxygen, nitrogen and phosphorus, are expressed as a percentage of the dry weight in table 8.

TABLE 8

Elemental composition of the phospholipid being studied.

| | % of the dry weight of phospholipid | |
|---|---|---|
| Element | Calculated (a) | Experimental |
| Carbon | 62.20 | 56.00 |
| Hydrogen | 9.89 | 9.20 |
| Oxygen | 22.61 | 23.27 |
| Nitrogen | 1.65 | 1.76 |
| Phosphorus | 3.65 | 3.40 |

(a) The theoretical values were calculated for the following formula: $C_{44}H_{84}O_{12}N_1P_1$.

The results of the compositional analysis of the phospholipid being studied and of the analysis by FAB mass spectrometry show that the eliciting phospholipid present in the mycelial extract of *Phytophthora capsici* is a sphingophospholipid containing inositol. It contains a nitrogen compound belonging to the sphingoid group and identified with $C_{16}$-sphingosine. The fatty acids present are represented by $C_{16}$, $C_{18}$, $C_{20}$ and $C_{22}$ saturated acids and $C_{18}$ and $C_{22}$ unsaturated acids. The latter exists in preponderant amounts. A $C_{22}$ hydroxylated and unsaturated acid has also been identified. The major compound has a molecular mass of 849. This result and the results of the elemental analysis demonstrate that this compound contains inositol, phosphorus, $C_{16}$-sphingosine and hydroxydocosenoic acid in the ratio 1:1:1:1.

C. STRUCTURAL STUDY OF THE PHOSPHOLIPID OF THE INVENTION

Figure 10A:
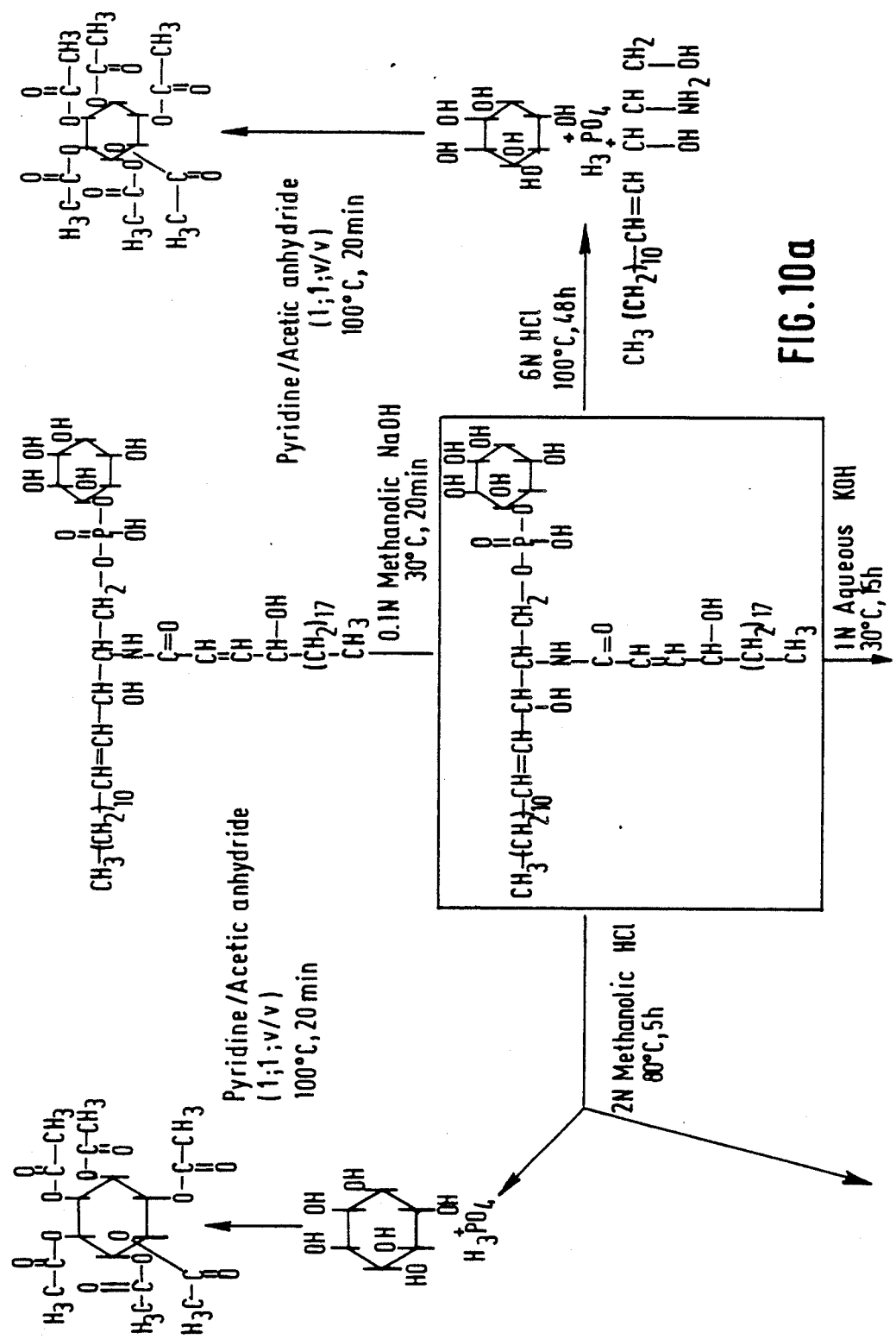
Figure 10B:
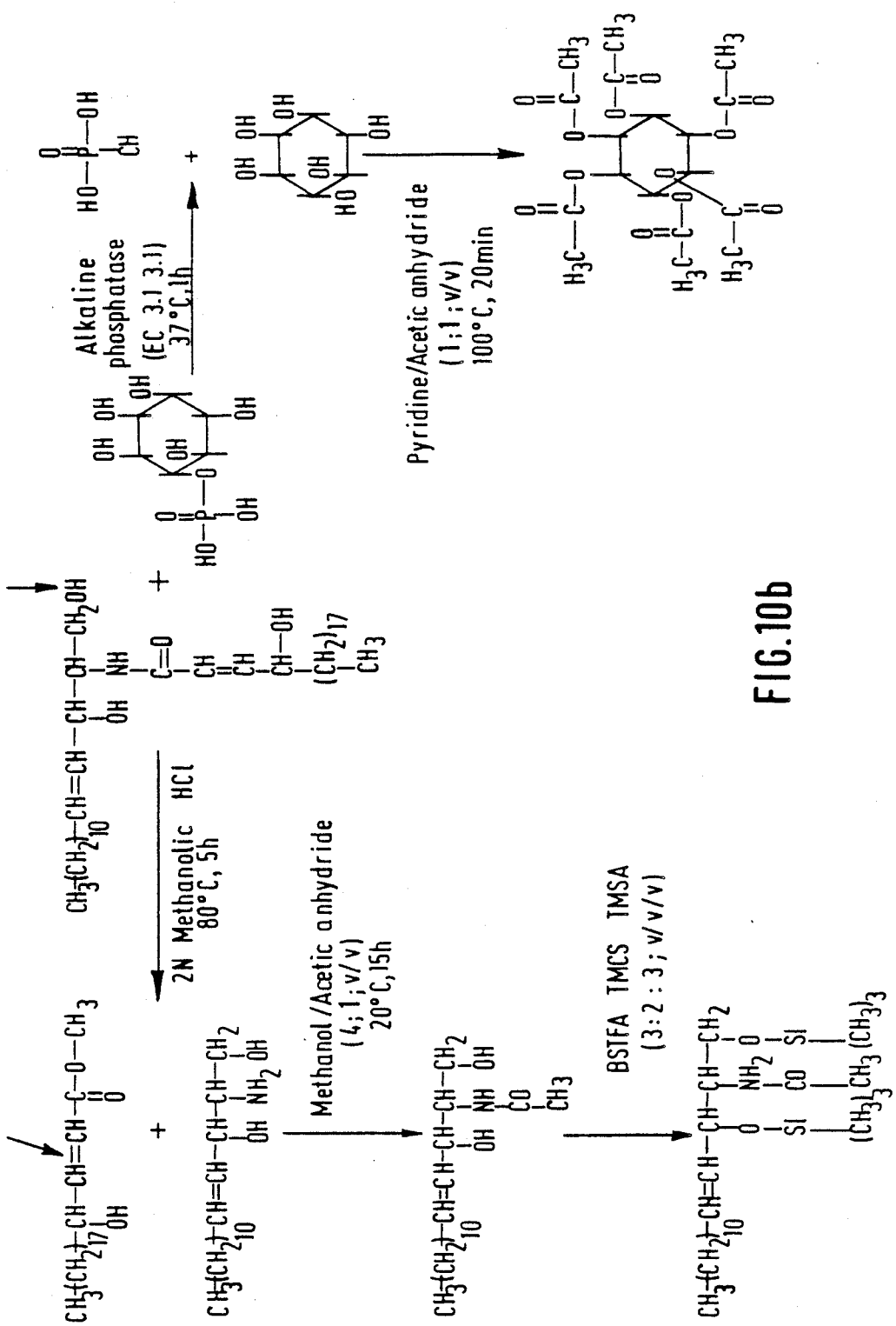

FIG. 10 summarizes the different stages of degradation of this phospholipid.

1. Analysis of the Phospholipid by Infrared Spectrometry

Figure 11:
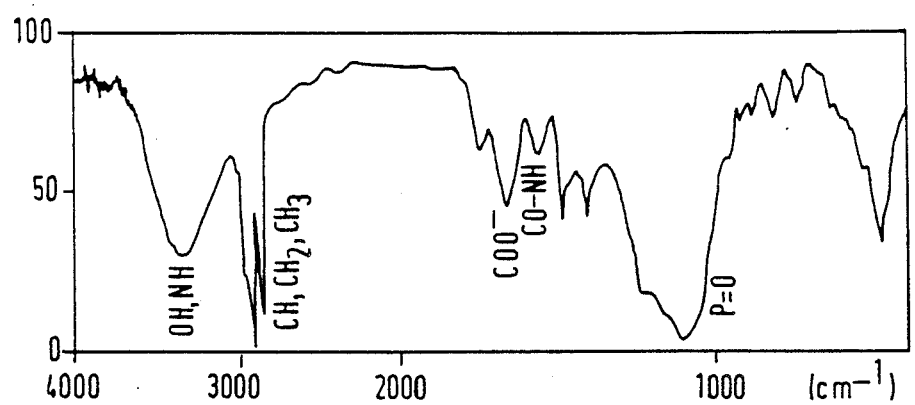
FIG. 11 is the infrared spectrum of phospholipid isolated from *Phytophthora capsici*.

The phospholipid isolated from *Phytophthora capsici* was analysed in the presence of control phospholipids by infrared spectrometry. The spectrum illustrated in FIG. 11 shows the presence of a hydroxyl band at 3400 $cm^{-1}$, bands at 2920, 2850 and 1645 $cm^{-1}$ characteristic of $CH_3$ and $CH_2$ radicals, a carbonyl band at 1730 $cm^{-1}$, a band characteristic of an amide bond at 1550 $cm^{-1}$ and a phosphoryl band at 1100 $cm^{-1}$.

2. Alkaline Hydrolyses of the Phospholipid of the Invention (a) Mild Alkaline Hydrolysis It was confirmed that the phospholipid of the invention, which contains a long-chain aminated base, is a sphingophospholipid. This phospholipid was subjected to an alkaline hydrolysis under the conditions of Smith and Lester [Journal of Biological Chemistry 249, 3395–3405 (1974)], these conditions not degrading phospholipids. It is hydrolyzed with 0.2N methanolic sodium hydroxide at 30° C. for 20 minutes. The reaction medium is neutralized with acetic acid and then extracted with chloroform. The chloroform extracts are analyzed by thin layer chromatography (HPTLC) in the solvent of Heape et al. After visualization with the reagent of Dittmer and Lester, modified by Vaskovsky and Kostetsky, it is found that the hydrolyzate gives a single spot of the same Rf as the corresponding native phospholipid.

Mild alkaline hydrolysis has hence not liberated any component of the phospholipid being studied, thereby demonstrating that the latter is a sphingophospholipid, for which the following two partial structures may be proposed:

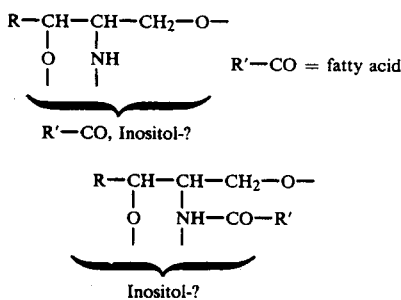

(1) R—CH—CH—CH₂—O—
        |    |
        O   NH        R'—CO = fatty acid
        |    |
        R'—CO, Inositol-?

(2) R—CH—CH—CH₂—O—
        |    |
        O   NH—CO—R'
        |
        Inositol-?

The position of the inositol was determined by FAB mass spectrometry.

(b) Saponification of the Phospholipid with 1N Aqueous Potassium Hydroxide

The phospholipid being studied was subjected to an alkaline hydrolysis under conditions which cleave the phosphate ester bond, liberating the ceramide and enabling the position of the inositol molecule to be specified.

4 mg of this phospholipid are saponified with 1.5 ml of 1N aqueous potassium hydroxide at 37° C. for 15 hours. After the mixture is cooled, the lipids are extracted with chloroform; the aqueous phase is neutralized with amberlite IRC-50.

(b-1) Analysis of the Water-Soluble Fraction

The aqueous phase of the 1N potassium hydroxide hydrolyzate is analyzed by gas chromatography, before and after hydrochloric acid hydrolysis, reduction and acetylation. A peak is observed whose retention time corresponds to that of inositol acetate only on the chromatogram obtained with the hydrolyzed extract. The alkaline hydrolysis of the phospholipid has hence not liberated the bond in which the inositol is engaged. It was demonstrated by the action of alkaline phosphatase that it was linked to the phosphate group.

The aqueous extract obtained after alkaline hydrolysis of the phospholipid is treated with alkaline phosphatase. The reaction medium is analysed by gas chromatography after reduction and acetylation. The presence of a peak corresponding to inositol acetate, a peak absent before enzymatic hydrolysis, is observed on the chromatogram obtained.

(b-2) Study of the Lipid-Soluble Fraction

(b-2α) Isolation of the Ceramide

The lipids present in the chloroform extracts are separated on a column of Bio Sil HA silicic acid with the following elution solvents: chloroform, chloroform/methanol containing from 5 to 50% of methanol. Each fraction collected is analyzed by thin layer chromatography on silica gel 60 (Merck 5628) in Karlson's solvent [Journal of lipid Research, 12, 466–472 (1971)] modified by Ohnishi [Agricultural and Biological Chemistry, 40, 1419–1423]. The fractions eluted with chloroform containing 25 to 50% of methanol contain the unhydrolyzed phospholipid, and the fractions eluted with chloroform contain the ceramide (Rf=0.69). The fatty acids have not been liberated, thereby demonstrating that the carboxyl group is not engaged in an ester bond in the phospholipid molecule. This enables the formula (1) to be eliminated and the above mentioned partial structure (2) to be proposed.

(b-2β) Methanolysis of the ceramide

Figure 12:
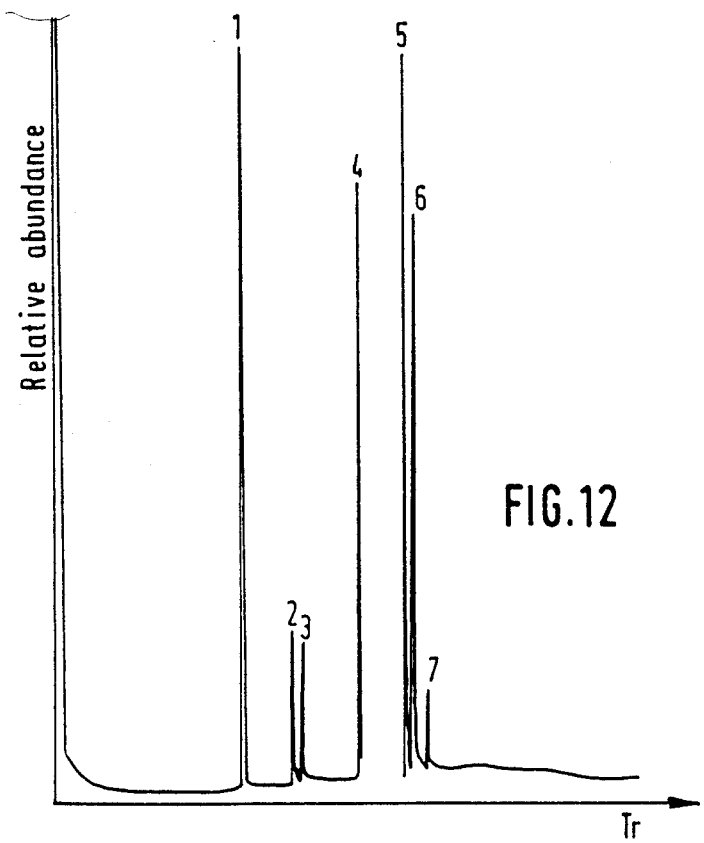
FIG. 12 is a chromatogram of the ceramide.

The methanolysis of the ceramide with 2N methanolic HCl at 80° C. under reflux for 5 hours liberates the aminated base extracted from the hydrolyzate by chloroform after alkalinization of the medium and identified by HPTLC with $C_{16}$-sphingosine, and fatty acids. The latter are analysed by gas chromatography of the methyl esters. The chromatogram illustrated in FIG. 12 shows that the ceramide contains the same fatty acids as the phospholipid of the invention, and in the same proportions.

TABLE 9

Comparative analysis of the content of fatty acids present in the ceramide and the phospholipid of the invention, which are derived from *Phytophthora capsici*

| Fatty acids identified | Mol % of the total fatty acids | | |
|---|---|---|---|
| | Ceramide | Phospholipid of the invention | Peak No. |
| Hexadecanoic acid | 23.0 | 26.2 | 1 |
| Octadecenoic acid | 3.7 | 5.7 | 2 |
| Octadecanoic acid | 2.9 | 2.8 | 3 |
| Eicosanoic acid | 15.0 | 11.6 | 4 |
| Docosenoic acid | 34.2 | 33.2 | 5 |
| Docosanoic acid | 18.0 | 16.1 | 6 |
| Hydroxydocosenoic acid | 3.2 | 4.3 | 7 |

(b-2γ) Study of the Ceramide by Mass Spectrometry

An analysis of the ceramide by MS/MS FAB mass spectrometry enabled its structure to be determined.

The mass spectra obtained show molecular peaks at m/z=608, 606 and 592 with positive FAB and at m/z=608 606, 604 and 590 with negative FAB. This indicates the presence of compounds of mass $M_1=607$ d, $M_2=609$ d, $M_3=605$ d and $M_4=591$ d (Table 10 below). The intensity of the peaks shows that the predominant compound has a mass of 607 daltons. An analysis of the molecular ions obtained in the positive and negative mode is carried out by mass spectrometry.

TABLE 10

Distribution of ions of similar molecular mass in the mass spectra

| $M_\gamma$ | EI | FD | FAB(+) | FAB(−) | Fragment |
|---|---|---|---|---|---|
| 256.2 | 256.2 | | | 255.2 | Palmitic acid |
| | | | | 404.2 | (PA + TEA—H)⁻ |
| 264.2 | 284.2 | | | 283.2 | Stearic acid |
| | | | | 432.2 | (SA + TEA—H)⁻ |
| 591.6 | | 592.4 | 592.4 | | $M_4H^+$ (610-$H_2O$)⁺ |
| | | | 574.4 | | (MH—$H_2O$)⁺ |
| | | | | 590.4 | (M—H)⁻ |
| 605.6 | | 606.5 | 606.4 | | $M_3H^+$ |
| | | 592.5 | | | (MNa—2$H_2O$)⁺ |
| | | | 588.4 | | (MH—$H_2O$)⁺ |
| | | | | 604.5 | (M—H)⁻ |

TABLE 10-continued

Distribution of ions of similar molecular mass in the mass spectra

| $M_\gamma$ | EI | FD | FAB(+) | FAB(−) | Fragment |
|---|---|---|---|---|---|
| 607.6 | | 608.4 | 608.4 | | $M_1H^+$ |
| | | 594.5 | | | $(MNa-2H_2O)^+$ |
| | | 590.5 | 590.4 | | $(MH-H_2O)^+$ |
| | | | 572.3 | | $(MH-2H_2O)^+$ |
| | 571.5 | | | | $(M-2H_2O)^+$ |
| | | | | 606.4 | $(M-H)^-$ |
| 609.5 | (610) | (610) | | | $M_2H^+$ (weak) |
| | 573.6 | | | | $(M-2H_2O)^+$ |
| | | | | 608.5 | $(M-H)^-$ |
| 607-Ac, | | | 734.4 | | $M_1(AC)_3H^+$ |
| | | | 674.4 | | $(MH-HOAc)^+$ |
| | 673.5 | | | | $(M-HOAc)^+$ |
| | | | 614.3 | | $(MH-2HOAc)^+$ |
| | 613.5 | | | | $(M-2HOAc)^+$ |
| | | | 596.3 | | $(MH-2HOAc-H_2O)^+$ |

Figure 13:
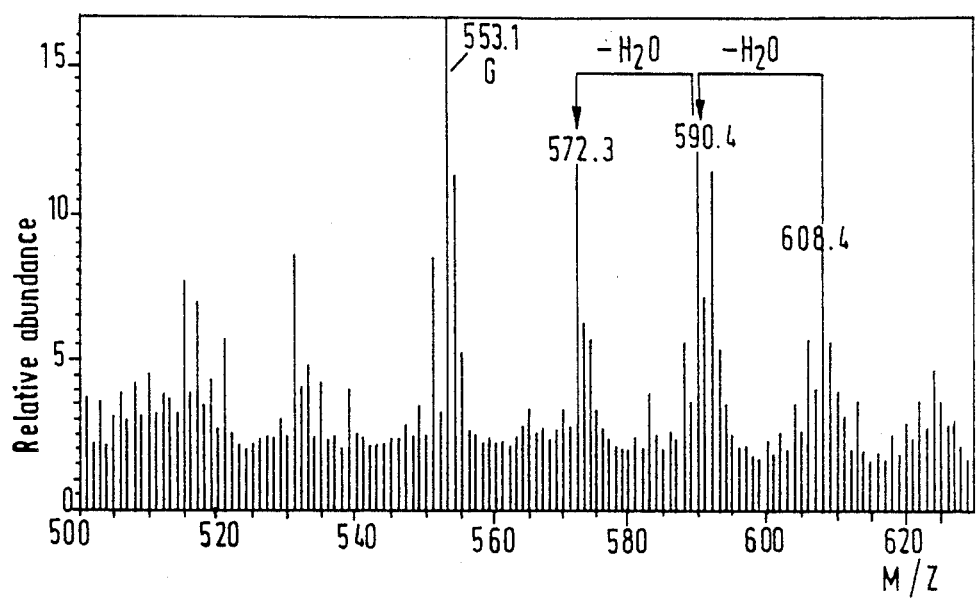
FIGS. 13, 15a and 15b show fragmentation with positive FAB.
Figure 15A:
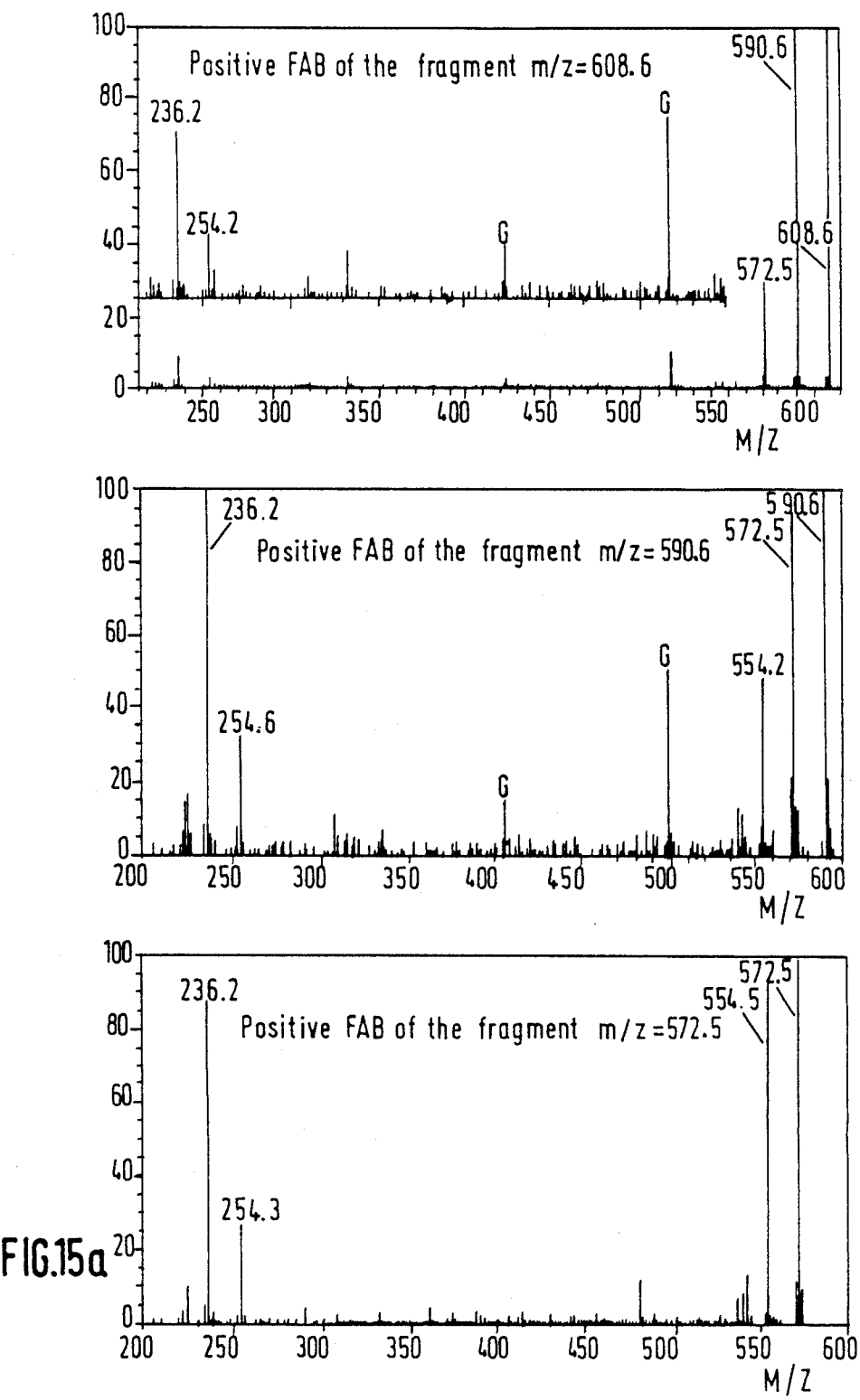
Figure 15B:
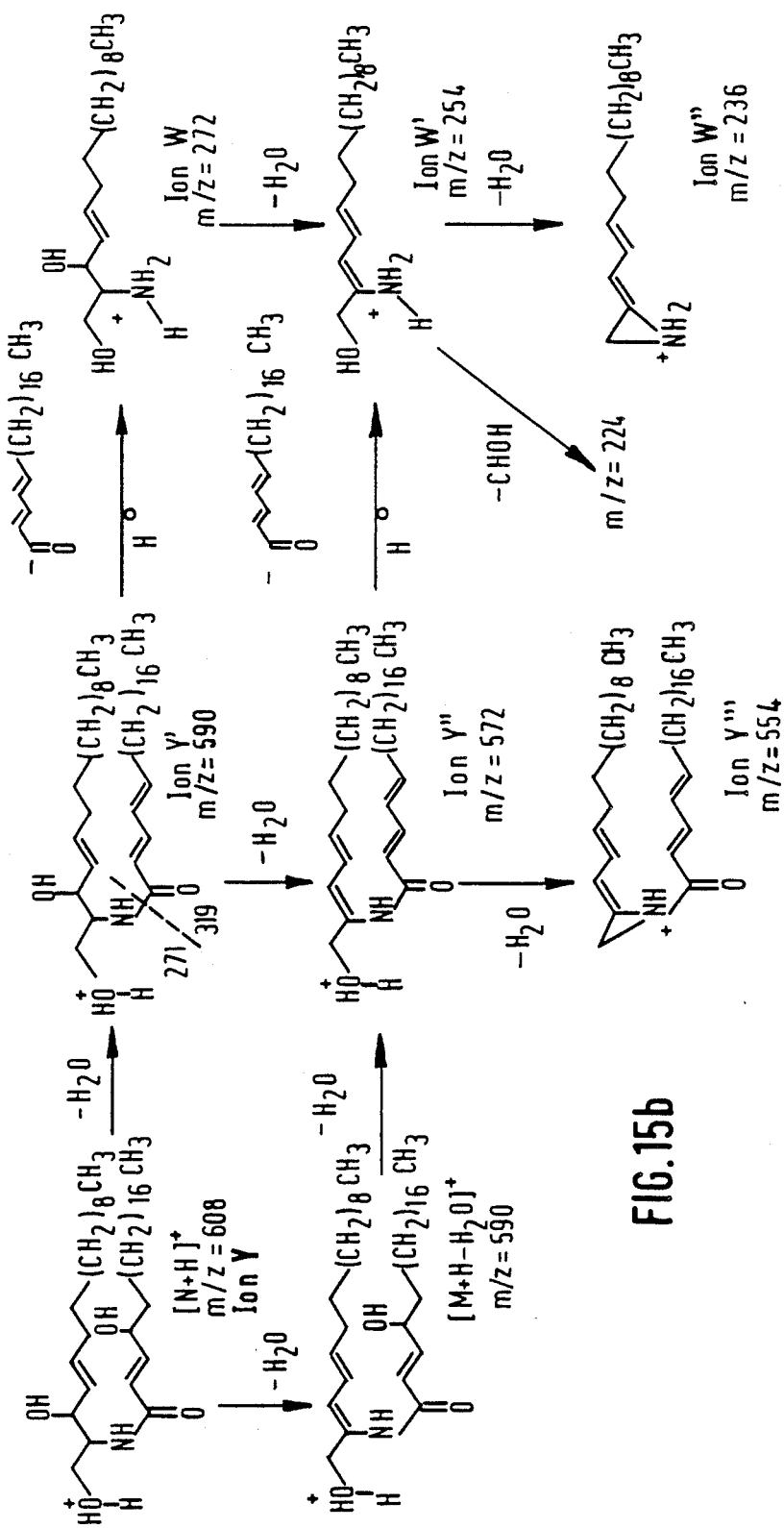

$M_1 = 607$
$M_2 = 609$
$M_3 = 605$
$M_4 = 591$
PA: Palmitic acid
SA: Stearic acid With positive FAB, the fragmentation (FIG. 13) gives the molecular ion $(M+H)^+$ at m/z=608 (ion Y) and the peaks at m/z=590, 572 and 554 originating from the departure of water and corresponding to the ions Y', Y'' and Y'''' (FIGS. 15a and 15b).

The ion W at m/z=272, obtained after cleavage of the amide bond and removal of the fatty acid, is absent, but the peaks are observed at m/z=254 and 236, which are derived therefrom by the removal of two water molecules. This fragment confirms the presence of $C_{16}$-sphingosine in the ceramide (M=607 d).

Figure 16A:
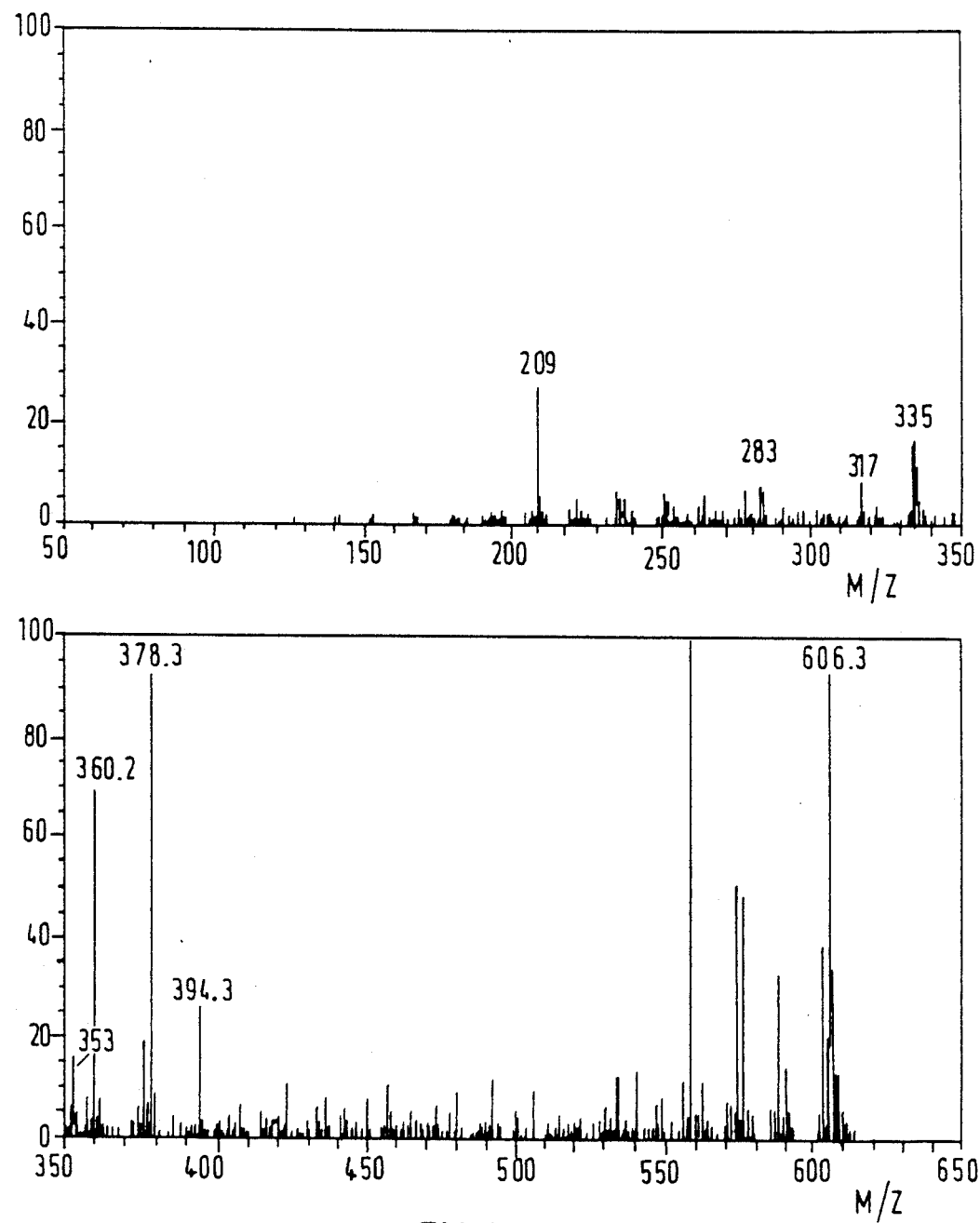
Figure 16B:
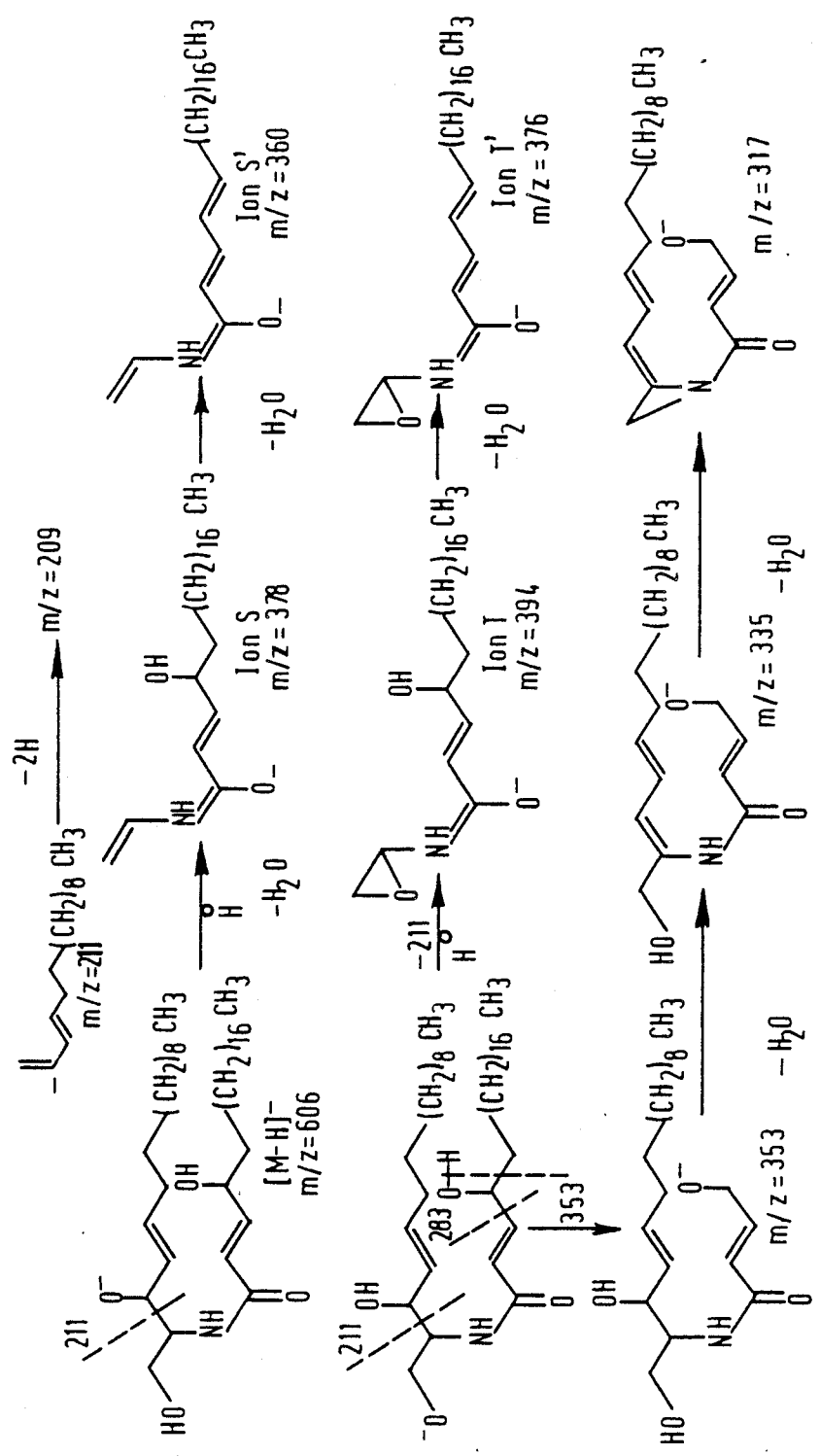
FIG. 16b ashows a large fragmentation of the sphingosine.

A large fragmentation (FIG. 16b) between carbon atoms 2 and 3 of the sphingosine gives, by loss of the fragment $(CH_3-(CH_2)_{10}-CH=CH-CHOH)^-$, the peaks of the T series and of the S series corresponding to $(M-211-2H)^-$ at m/z=394, and to $(M-211-H_2O)^-$ at m/z=378; a second series of T' peaks at m/z=376 and S' peaks at m/z=360 results from the loss of a water molecule. These fragments show that the fatty acid molecule present in the ceramide (M=607) is a hydroxylated and monounsaturated $C_{22}$ molecule.

Figure 14:
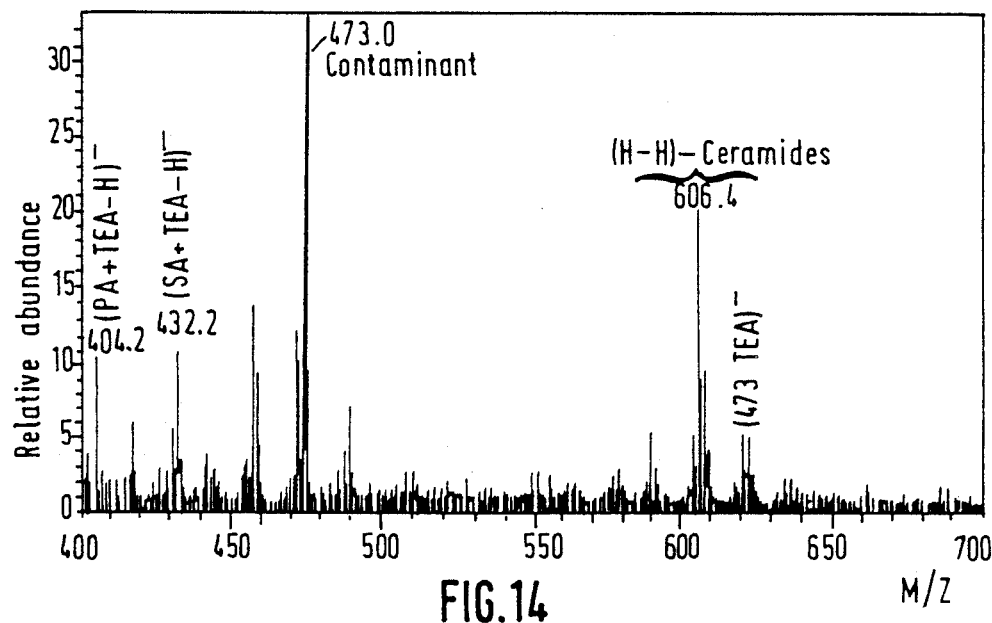
FIGS. 14 and 16A show spectra obtained with negative FAB.

In the spectra obtained with negative FAB (FIGS. 14 and 16a), the presence is observed, in addition, of peaks of low intensity which are located at m/z=283 and 353 and which result from the cleavage on both sides of a hydroxyl group situated at $C^4$ in the carbon chain of the fatty acid.

These results determine the position of the hydroxyl and of the double bond in the fatty acid present in the ceramide (M=607). The acid in question is 4-hydroxy-2-docosenoic acid. The presence of two hydroxyls in the ceramide molecule was confirmed by analysis of the acetylated ceramide. Table 11 gives the results obtained for the preponderant compound corresponding to the ceramide having a molecular mass of 607 d, and the other compounds present in smaller amounts. The value for the ions (Y, W, V, T, S) corresponding to the different fragmentations shows the presence in each of these ceramides of $C_{16}$-sphingosine and of the monohydroxylated and saturated ($M_2=609$), monohydroxylated and diunsaturated ($M_3=605$) and monounsaturated (M=591) $C_{22}$ fatty acid.

TABLE 11

Values observed for the MS/MS CID FAB of the ceramide

| $M_\gamma$ | 609 | | 607 | | | 605 | |
|---|---|---|---|---|---|---|---|
| Ion (+) | 610 | 592* | 608 | 590 | 572 | 605 | 588 |
| Y | | (592) | (608) | | | (606) | |
| Y' | | 574 | 590 | (590) | | 588 | (588) |
| Y'' | | 556 | 572 | 572 | (572) | 570 | 570 |
| Y''' | | | | 554 | 554 | | 552 |
| V** | | | | | | | |
| V'** | | | 332 | | (332) | (330) | |
| ? | | 316 | | | | | |
| W** | | 274 | | | | | |
| W' | | 256,254 | 254 | 254 | 254 | | 254,252 |
| W'' | | 238,236 | 236 | 236 | 236 | 236 | 236,234 |
| Ion(−) | 608 major-minor | | 606 | | | 604 | |
| S | 378 | 380 | 378 | | | | |
| S' | 360 | 362 | 360 | | | | |
| T | (394) | (396) | 394 | | | | |
| T' | 376 | (378) | 375 | | | | |

*$M_1 = 591$ ($MH^+ = m/z = 592$) may result from the dehydration of m/z = 610 or may be present in the sample before analysis In either case, the hydroxyl group located on the N-acylating substituent is the first to be removed.

**Note:
these ions are observed only in the MS/MS mass spectra of ceramides and cerebrosides containing a saturated base.

3. Conclusion: Structure of the Phospholipid of Formula (Ia)

The phospholipid isolated from the mycelium of *Phytophthora capsici* is a sphingophospholipid containing inositol (M=849 d) containing an unsaturated long-chain base: $C_{16}$-sphingosine, 4-hydroxy-2-docosenoic (or γ-hydroxydocosenoic) acid, phosphorus and inositol. Its structure is as shown above. The fatty acid amidates the amino group of the sphingosine; the position of the inositol phosphate is given by analogy with known structures [Smith et al., Journal of Biological Chemistry, 249, 3395-3405 (1974); Hackett et al., F.E.B.S. Letters, 74, 259-263 (1977)].

Less abundant sphingophospholipids containing inositol, defined in the preamble of the present description, different from the phospholipid (Ia) in the nature of the fatty acid, have also been identified.

EXAMPLE 2—TESTING FOR THE PHOSPHOLIPID OF THE FORMULA (Ia) IN THE LYOPHILIZED MYCELIUM OF *Phytophthora capsici* STRAINS 197 and 15.12 A A washing according to the method of Folch et al. (Journal of Biological Chemistry, 226 497–509) with a chloroform/methanol/water (40:20:15; v/v/v) mixture and a filtration on n°3 sintered glass enables 14.4% of Lipids present in *Phytophthora capsici* 197 and 13.3% in *Phytophthora capsici* 15.12 A to be isolated, these percentages being calculated with respect to the lyophilized mycelium.

These lipids were chromatographed on a column of Mallinckrodt silicic acid mixed with Celite 545 in a (3:1; m/m) ratio. Three fractions are collected, $OEM_I$, $OEM_{II}$ and $OEM_{III}$, eluted with chloroform, chloroform/methanol (75:5; v/v) and chloroform/methanol (50:50; v/v), respectively. These fractions represent 12.2%, 1.7% and 0.3%, respectively, with respect to the lyophilized mycelium in the case of extraction of the mycelial lipids of *Phytophthora capsici* strain 197, and 11.2%, 1.9% and 0.2%, respectively, with respect to the lyophilized mycelium in the case of the extraction of mycelial lipids of *Phytophthora capsici* strain 15.12 A.

The fractions $OEM_I$, $OEM_{II}$ and $OEM_{III}$ were analysed by chromatography on silica gel 60 plates (Merck 5628). After migration in the solvent of Heape et al. and visualization with the reagent of Dittmer and Lester modified by Vaskovsky and Kostetsky, the absence is noted of a spot of Rf/Ptd Ins=0.76 having the same behavior as the phospholipid of the formula (Ia) deposited as a control.

These results show that the phospholipid not released by a simple washing of the mycelium according to Folch's method is an intrinsic constituent of the fungal cell.

EXAMPLE 3: LOCALIZATION OF THE PHOSPHOLIPID OF THE FORMULA (Ia) IN THE FUNGAL CELL OF *Phytophthora capsici* STRAINS 197 and 15.12 A The combination of operations performed is illustrated as follows.

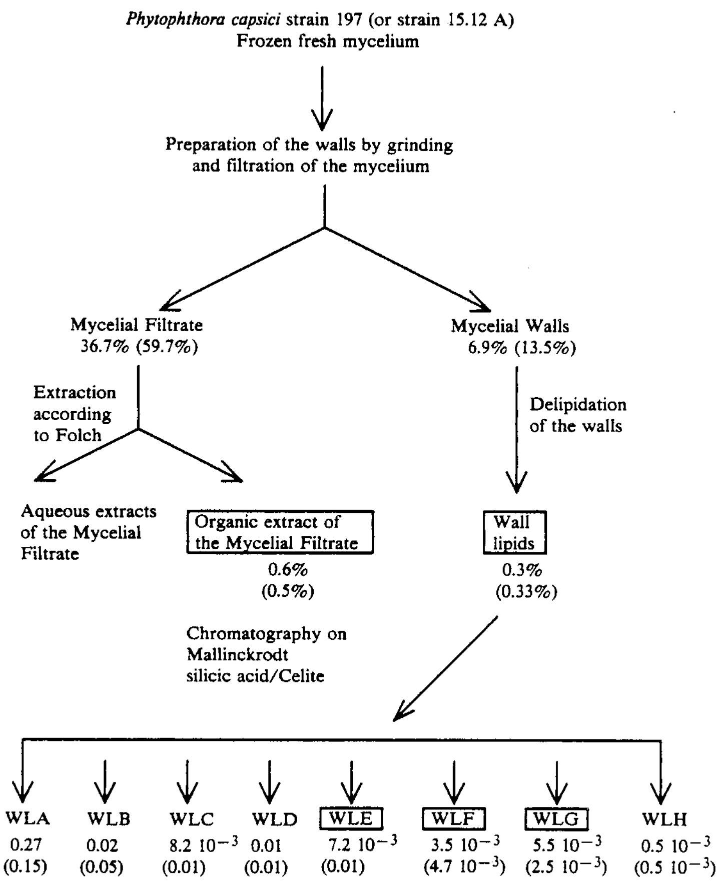

. The yields are shown as % of the frozen fresh mycelium
. The framed fractions contain the phospholipid of the formula (Ia)
. The values shown in brackets relate to the fractionation of the mycelium of *Phytophthora capsici* strain 15.12 A.

The different cell fractions are obtained by grinding the fresh mycelium suspended in 0.1M potassium phosphate buffer, pH 7.2, for 10 minutes at 20° C. After washing of the ground preparation and filtration, the crude mycelial walls, representing 6.9% and 13.5% of the fresh mycelium for strains 197 and 15.12 A, respectively, are collected. The non-sedimented fractions represent 36.7% of the mycelium of strain 197 and 59.7% of the mycelium of strain 15.12 A.

Figure 17:
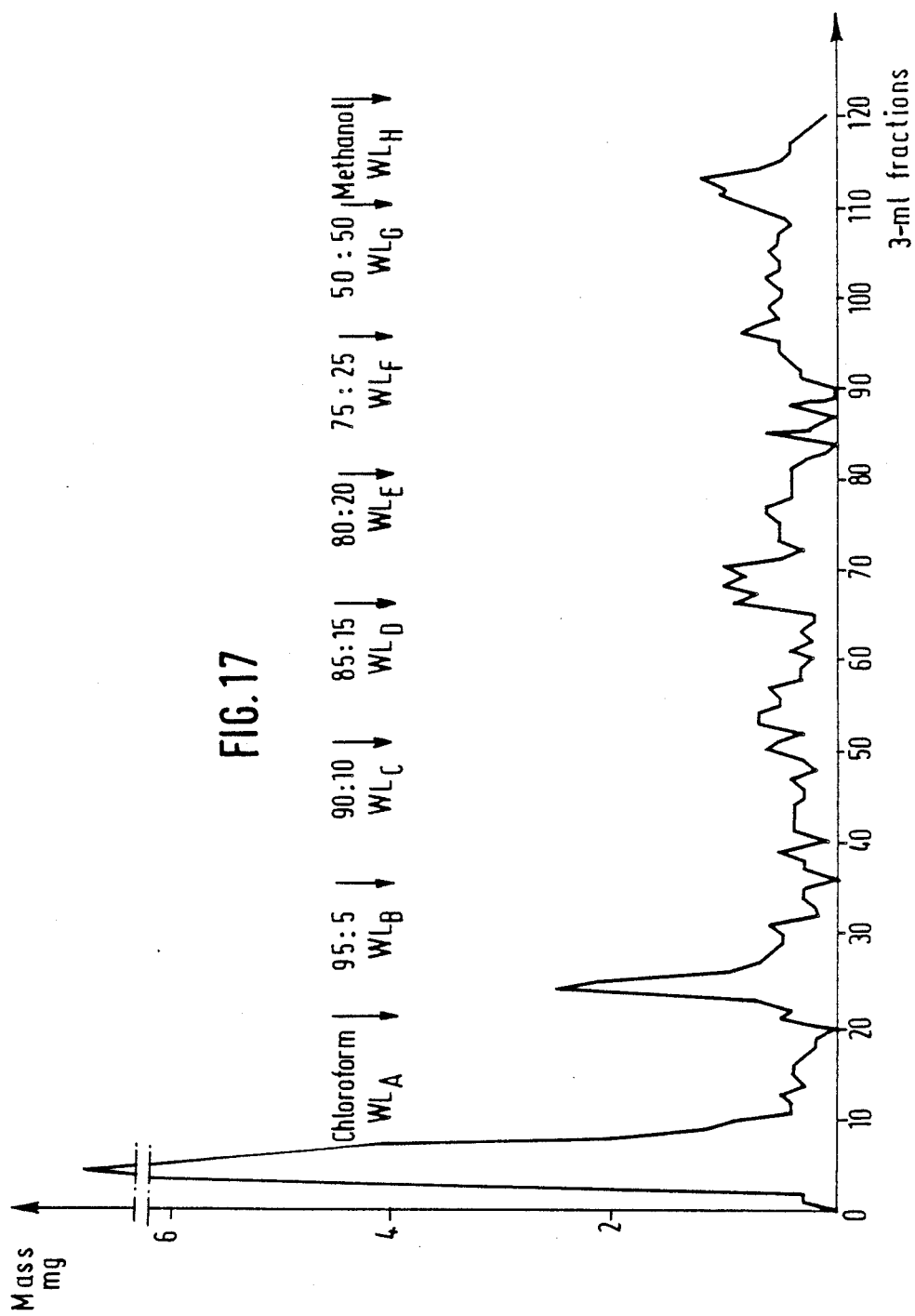
FIGS. 17 and 18 show elution profiles of the lipids.
Figure 18:
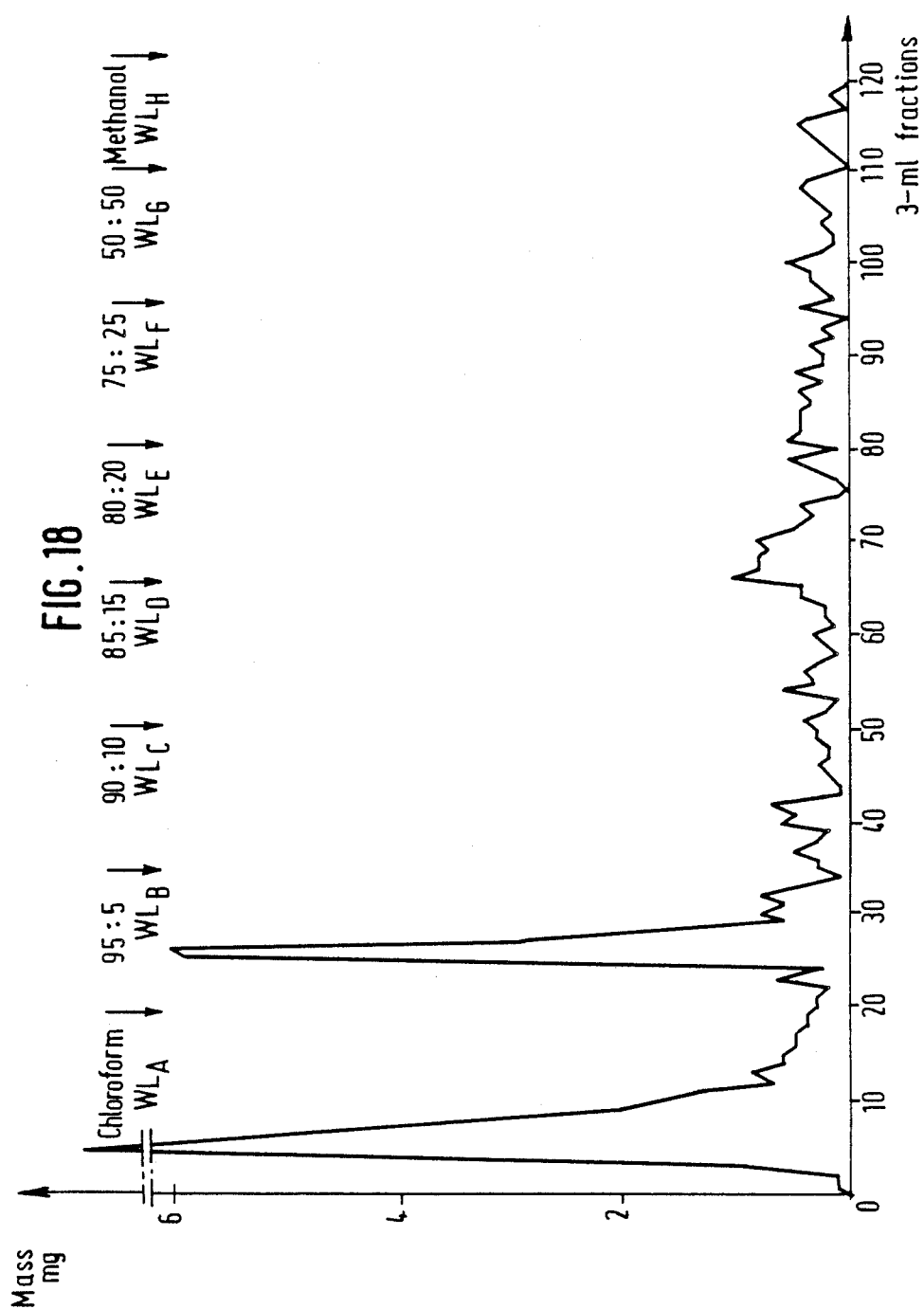

The lipids present in these fractions are extracted for 48 hours with a chloroform/methanol/water (40:20:15; v/v/v) mixture. They represent 0.6 and 0.5% of the fresh mycelium of strains 197 and 15.12 A of the *Phytophthora capsici*. A delipidation of the walls is performed with a chloroform/methanol (2:1; v/v) mixture. The lipids obtained represent 0.3% of the fresh mycelium for the two strains studied. They are fractionated by chromatography on a column of Mallinckrodt silicic acid/Celite 545 (3:1; m/m). Eight fractions are eluted with increasing contents of methanol in chloroform. The elution profiles of the lipids are shown in FIGS. 17 and 18. Each of the fractions isolated is analysed by thin layer chromatography on silica gel 60 (Merck 5628) in the solvent of Heape et al., in the presence of the phospholipid of formula (Ia) as a control. The reagent of Dittman and Lester modified by Vaskovsky and Kostetsky demonstrates the presence of a phospholipid of formula (Ia) in the organic extracts of the mycelial filtrate, and also in the wall lipids $WL_E$, $WL_F$ and $WL_G$ of the two strains. This study shows that the phospholipid of formula (Ia) is a component of the mycelial wall, of which it represents 5 to 10% of the lipids.

In the same way, the sphingophospholipid of formula (Ia) was also found in the fungal wall of *Phytophthora parasitica* strain 26. In contrast, it was absent in *Ophiobolus graminis*.

EXAMPLE 4

The general procedure used for monitoring the biological activity of the fractions isolated will be described below, such monitoring being carried out on the cotyledons of a variety of capsicum sensitive to *Phytophthora capsici*: the capsicum Yolo Wonder.

A—INCUBATION OF THE CAPSICUM COTYLEDONS

The cotyledons are kept alive on water, the upper face of the limb being in contact with the liquid. 12.5 μg of the fraction, taken up with 25 μl of water, are deposited on the lower face. The drops are absorbed in 24 hours.

B—INDUCTION OF RESISTANCE

10 μl of a suspension of zoospores of *Phytophthora capsici* (62,500 zoospores/ml) are placed without damaging the tissues at the same point as the microdrop of fraction. Incubation is carried out at 22° C. with 16 h of light. The first symptoms are assessed starting on day 3 and up to day 7, according to the following scale:
score 0: no symptoms
score 1: presence of small necrotic points without subsequent development
score 3: appearance of a necrosis spreading to the whole cotyledon.

The added scores are expressed as percentages, 100% corresponding to all the cotyledons assigned a score of 3. Each replicate contains 15 cotyledons.

The capacity of the phospholipid of formula (Ia) to induce a protection in capsicum with respect to its pathogen could be demonstrated in this manner. It was, moreover, shown that, while inositol phosphate is completely incapable of inducing a protection of capsicum, the ceramide derived from the phospholipid retains a resistance-inducing activity at high concentrations.

The effect of the concentration of the phospholipid of the invention on the resistance-inducing activity was also studied.

Figure 19:
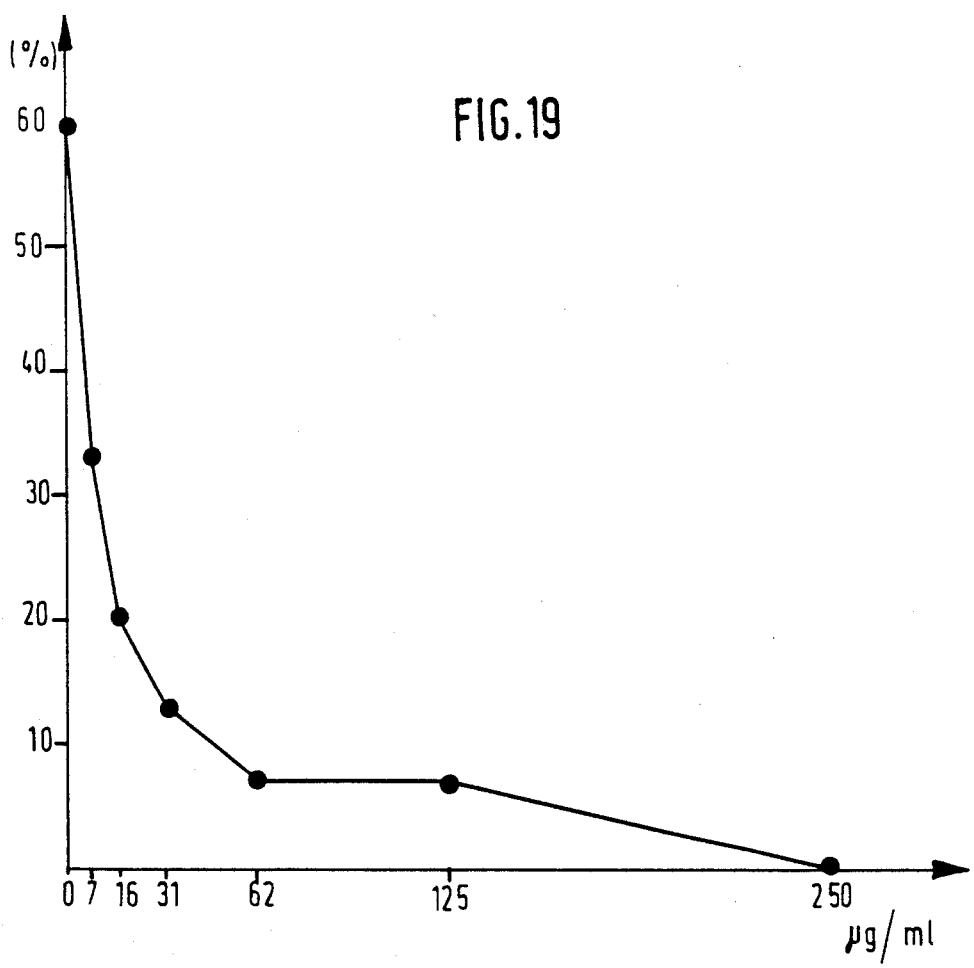

The phospholipid of formula (Ia) was applied on the capsicum Yolo Wonder at increasing concentrations. The results illustrated in FIG. 19 show that the sensitivity of the capsicum cotyledons with respect to *Phytophthora capsici* (as ordinates) decreases rapidly with an increase in the concentration of the solution of phospholipid of formula (Ia) which is applied to it (as abscissae). A sensitivity of 100% corresponds to a total absence of resistance; in contrast a sensitivity of 0% corresponds to a total resistance. The sensitivity of the capsicum to its pathogen decreases by half after application of 7 μg/ml of phospholipid; the protective effect is maximal for doses of phospholipid of formula (Ia) varying from 50 to 250 μg/ml.

EXAMPLE 5: APPLICATION OF THE FUNGAL ELICITOR OF THE INVENTION ON VARIOUS PLANTS

A—PLANT MATERIAL

Various market-garden plants were used: melon (variety Vedrantais), tomato (variety Monalbo) and capsicum (variety Yolo Wonder).

The seeds of market-garden plants are sown in pans, the germination and development of the seedlings up to the 1- to 2-leaf stage taking place under glass.

B—PROCEDURES FOR APPLICATION OF THE FUNGAL ELICITOR [COMPOUND OF FORMULA (Ia)]

The elicitor was applied to the plants in the following manner: instantaneous dipping of the sectioned end of a cotyledon into a solution of elicitor at a concentration of 100 μg/ml.

C—ARTIFICIAL CONTAMINATIONS DESIGNED TO DEMONSTRATE THE INDUCED STATE

To monitor the induced state of the aerial portion, different leaf parasites were used according to the plants being studied:

melon: *Pseudoperonospora cubensis* maintained on melon cotyledons kept alive on water at 18°-20° C. The sporangia are collected in water and their concentration is adjusted to 1,000/ml.

tomato: *Phytophthora infestans* (strain St. Etienne des Sorts) maintained on chick-pea oat medium. The sporangia are removed from 3-week old cultures and suspended in water at a concentration of 9,000/ml.

capsicum: *Phytophthora capsici* (strain 15) maintained alternately on V8 medium and on synthetic medium. The production of zoospores is carried out according to a technique described by Molot et al. in Ann. Phytopathol. 8 (4), pages 399-409 (1976). The concentration used is 20,000 zoospores/ml.

The parasites are applied by spraying onto the foliage and the plants are maintained in a moist chamber for 3 days.

D—SCORING

The assessment of the attack of the leaves by *P. cubensis*, *P. infestans* and *P. capsici* consists in assigning to each plant a score from 0 to 5, the cumulative totals being expressed as a percentage sensitivity.

All treatments theoretically comprise 3 or 4 replicates.

E—ANCILLARY TESTS SHOWING THE EFFECT OF THE ROOT EXUDATES OF THE ELICITED PLANTS ON THE SPOROGENESIS OF *P. CAPSICI*

Young capsicum or tomato seedlings are uprooted and, after their roots have been washed, they are set up again dipping into the nutrient solution (approximately three days) and then into a small amount of water (approximately 25 ml for 10 seedlings). During this latter operation, the end of a sectioned cotyledon is dipped instantaneously into the elicitor at a concentration of 100 μg/ml. After 72 hours, the water in which the roots were bathed is collected, filtered under sterile conditions (Seitz EKSI) and distributed in 1 ml portions into 12 cups in which a *P. capsici* agar culture implant (diam.=4 mm) is immersed; from this implant which contained only mycelium at the start, sporangia are formed rapidly (between 24 and 48 hours); their number may be assessed by counting under a binocular microscope at a magnification of 16 or 40.

F—RESULTS (a) Protection with respect to a few foliage parasites

TABLE 12

Resistance of a few market-garden plants to various foliage parasites after eliciting by the instantaneous dipping of a cotyledon end into the phospholipid containing inositol (100 μg/ml)

| | % sensitivity of: | | |
|---|---|---|---|
| | Melon (Vedrantais) to *Pseudoperonospora cubensis* | Tomato (Monalbo) to *Phytophthora infestans* | Capsicum (Yolo Wonder) to *Phytophthora capsici* |
| Water control | 52 ± 5.1 | 41 ± 2.7 | 47 ± 3.5 |
| Phospholipid containing inositol of the invention | 40 ± 5.3 | 35 ± 2.4 | 23 ± 6.1 |

A score from 0 to 5 expressing the severity of the symptoms is assigned to each plant. The cumulative totals are expressed as a percentage sensitivity.

Irrespective of which system is used (melon—*Pseudoperonospora cubensis*; tomato—*Phytophthora infestans*; capsicum—*Phytophthora capsici*), the foliage of the elicited seedlings always proves to be better protected than that of the controls with respect to cryptogamic attacks.

(b) Effect of the root exudates on the sporogenesis of *P. capsici*

TABLE 13

Average number of sporangia of *Phytophthora capsici* obtained from a calibrated mycelial implant immersed in a root exudate of seedlings elicited with the phospholipid containing inositol (100 μg/ml)

| | | Capsicum exudate | | Tomato exudate | |
|---|---|---|---|---|---|
| | | NA | A | NA | A |
| Cotyledon damaged and dipped in. | Water | 47 | 92 | 66 | 129 |
| | Phospholipid containing inositol of the invention | 20 | 102 | 236 | 584 |
| Undamaged cotyledon | | 100 | 131 | 108 | 165 |
| Water control | | 68 | 27 | 68 | 27 |

NA = exudate not autoclaved
A = exudate autoclaved (20 minutes at 120° C.)

The water in which roots of capsicum or of tomato seedlings, elicited on an aerial organ, have dipped for 72 hours is capable of stimulating or inhibiting the formation of sporangia by the parasite.

Compared with the control damaged and treated with water, the exudates originating from undamaged (and hence unelicited) plants exert a stimulatory effect on sporogenesis; the simple fact of damaging the cotyledon and dipping it instantaneously in water reduces the number of sporangia.

If eliciting is performed on the wound, it is possible to observe either a stimulatory effect in the case of tomato, or an inhibitory effect in the case of capsicum.

After autoclaving, the water into which the roots dipped all become favorable to sporogenesis. In contrast, pure water (little oxygenation of the medium, precipitation of inorganic salts) proves less favorable.

These results suggest the existence, in the root exudates, of heat-labile substances released by the plant in response to eliciting, and capable of exerting considerable influence on the biology of the parasite.

G—TESTS IN GLASSHOUSE (a) On Wheat

After having impregnated Lutin wheat seed for a period of time of less than 48 hours by the phospholipid of formula (Ia) at a concentration of 1 μg/ml, a stimulatory effect on the height of the plants to maturity and on the time required for maturity, i.e. the space of time between the flowering date and the date of maturity, is observed. (From an agricultural point of view, it is best to have the time increased).

The results are recorded in Table 14:

TABLE 14

Physiological effect on the Lutin wheat of the treatment of the seed by impregnation.

| | Average height of the plant (mm) | Time required for maturity (days) |
|---|---|---|
| Control (water) | 704 | 30.5 |
| Phospholipid (Ia) | 715 | 32.8 |

(b) On Corn

After having impregnated seed of corn belonging to Sabrina and Carola cultivars by the phospholipid (Ia) (10 μg/ml), for a period of time having not exceeded 48 hours, an increase of the plant weight is observed. The results are recorded on Table 15.

TABLE 15

|  | Weight of a plant (g) | |
|---|---|---|
|  | Sabrina | Carola |
| Control (water) | 219 | 180 |
| Phospholipid (Ia) | 235 | 248 |

H—TESTS IN FIELD

(a) On Corn

After having impregnated seed of corn belonging to Carola cultivar by the phospholipid (Ia) (concentration of 10 μg/ml), for a period of time having not exceeded 48 hours, an increase in the precocity of flowering of 1½ day by comparison with the control (corn the seed of which had been soaked in water for the same period of time) is observed.

(b) On Wheat

An aqueous suspension of the phospholipid of the formula (Ia) at a concentration of 25 μg/ml was sprayed on wheat of Lutin cultivar at the beginning of bolting.

In the healthy zone, not artificially contaminated by the take all disease (*Gaemannomyces graminis*), an increase of the yield of about 8% by comparison with the control is observed. This tendency is confirmed when the progress of the focuses of disease from the next infested parcel is investigated; the disease progresses of 20 cm in the untreated parcels and only of 15 cm in the treated parcels.

Various physiological modifications are also observed:

the size of the wheat is increased (the average height of the plant is of 86 cm, while it is only of 84 cm for the control);

the wheat shows an advance of flowering precocity; and, a decrease of the sensitivity of the wheat to oidium (*Erysiphe graminis*) is observed: the score is of 16 in the case of the treated wheat, while it is of 17 in the case of the control. (Score of sensitivity to oidium in natural infection: from 0 to 40).

What is claimed is:

1. A sphingophospholipid containing inositol and represented by general formula (1):

$$CH_3-(CH_2)_{12}CH=CH-\underset{OH}{CH}-\underset{\underset{\underset{O}{\parallel}}{\underset{C}{|}}}{\underset{NH}{CH}}-CH_2-O-\underset{\underset{OH}{|}}{\overset{\overset{O}{\parallel}}{P}}-O-\text{(inositol)} \quad (I)$$

in which Z denotes the residues:

$$CH_3-(CH_2)_{17}-\underset{OH}{\underset{|}{CH}}-CH=CH-;$$

$$CH_3-(CH_2)_{19}-\underset{OH}{\underset{|}{CH}}-;$$

-continued $$CH_3-(CH_2)_{n1}-CH=CH-(CH_2)_{m1}-\underset{OH}{\underset{|}{CH}}-CH=CH-,$$

with $0 \leq n1 \leq 15$; $0 \leq m1 \leq 15$ and $n1+m1=15$; and
$CH_3-(CH_2)_{n2}-CH=CH-(CH_2)_{m2}-$, with $0 \leq n2 \leq 18$; $0 \leq m2 \leq 18$, and $n2+m2=18$.

2. Sphingophospholipids containing inositol represented by the formula (I), as defined in claim 1, in which Z denotes $$CH_3-(CH_2)_{17}-\underset{OH}{\underset{|}{CH}}-CH=CH-.$$

3. All sphingolipid fraction consisting of a mixture of at least two different compounds of formula (I), as defined in claim 1.

4. A sphingolipid fraction consisting of a major proportion of the compound of formula (I) as defined in claim 1, in which Z denotes $$CH_3-(CH_2)_{17}-\underset{OH}{\underset{|}{CH}}-CH=CH-,$$

and a minor proportion of at least one other compound of formula (I) as defined in claim 1.

5. A method of preparing a sphingolipid fraction consisting of a mixture of at least two different compounds of formula (I), as defined in claim 1, and for preparing a compound of formula (I), as defined in claim 1, which sequentially comprises:
 (a) preparing a mycelial extract of Phytophthora, the said extract showing a resistance-inducing activity in a plant capable of being infested by a pathogen belonging to the species Phytophthora;
 (b) extracting the total lipids of the mycelial extract;
 (c) fractionating the lipids by adsorption chromatography on silicic acid, in order to collect fractions retaining a major part of the initial activity; and, optionally,
 (d) purifying further to produce a desired compound of formula (I).

6. A method for preparing a sphingolipid fraction consisting of a mixture of at least two different compounds of formula (I), as defined in claim 1, or for preparing a compound of formula (I), as defined in claim 1, which comprises extracting mycelial lipids of Phytophthora to obtain the fraction, and, optionally, purifying further to produce a desired compound of formula (I).

7. A method for preparing a sphingolipid fraction consisting of a mixture of at least two different compounds of formula (I), as defined in claim 1, or for preparing a compound of formula (I), as defined in claim 1, which sequentially comprises:
 (a) grinding mycelium of Phytophthora in a liquid medium, and filtering the obtained suspension to collect crude mycelial walls and a mycelial filtrate, which constitute desired fractions,
 (b) extracting the wall lipids, the lipids also constituting desired fractions, and, optionally,
 (c) purifying the previously-mentioned fractions further to produce a desired compound of formula (I).

8. A method as claimed in one of claims 6 and 7, wherein each purification of a sphingolipid fraction is performed by adsorption chromatography on silicic acid.

9. A method as claimed in one of claims 5 to 7, wherein mycelium of *Phytophthora capsici* or of *Phytophthora parasitica* is used as starting material.

* * * * *